United States Patent
Magazzù et al.

(10) Patent No.: US 11,849,703 B2
(45) Date of Patent: Dec. 26, 2023

(54) RUMINAL BOLUS FOR TRACKING BOVINES

(71) Applicant: Movment LLC, Dover, DE (US)

(72) Inventors: Giuseppe Magazzù, prov. Bo. (IT); Dario Presti, Pisa (IT); Rosa Benedetto, Pisa (IT); Ramsey Bland, Jamestown, NY (US); Martin Hoch, Lakewood, NY (US)

(73) Assignee: Movment LLC zoo, Cracow (PL)

( * ) Notice: Subject to any disclaimer, the term of this patent is extended or adjusted under 35 U.S.C. 154(b) by 789 days.

(21) Appl. No.: 16/970,837

(22) PCT Filed: Feb. 19, 2019

(86) PCT No.: PCT/US2019/018600
§ 371 (c)(1),
(2) Date: Aug. 18, 2020

(87) PCT Pub. No.: WO2019/161397
PCT Pub. Date: Aug. 22, 2019

(65) Prior Publication Data
US 2020/0375148 A1  Dec. 3, 2020

Related U.S. Application Data

(60) Provisional application No. 62/632,158, filed on Feb. 19, 2018.

(51) Int. Cl.
*A01K 11/00* (2006.01)
*A61B 5/00* (2006.01)
(Continued)

(52) U.S. Cl.
CPC .......... *A01K 11/007* (2013.01); *A01K 11/008* (2013.01); *A01K 29/005* (2013.01);
(Continued)

(58) Field of Classification Search
CPC .... A01K 11/007; A01K 29/00; A01K 29/005; A01K 11/008; A61B 5/0008; A61B 5/01;
(Continued)

(56) References Cited

U.S. PATENT DOCUMENTS

| 11,710,562 B2 * | 7/2023 | Weydt | G16H 40/67 |
| | | | 604/503 |
| 2009/0182207 A1 * | 7/2009 | Riskey | A61B 5/1124 |
| | | | 600/587 |

(Continued)

FOREIGN PATENT DOCUMENTS

WO   WO-2019161397 A1   8/2019

OTHER PUBLICATIONS

"International Application Serial No. PCT/US2019/018600, International Search Report dated May 2, 2019", 2 pgs.

(Continued)

*Primary Examiner* — Yvonne R Abbott-Lewis
(74) *Attorney, Agent, or Firm* — Culhane Meadows PLLC; Michael P. Dunnam

(57) ABSTRACT

A bolus is inserted into the rumen of a bovine and includes sensors for collecting the temperature, activity level, and location of the animal over time and circuitry for communicating the collected data to a server that monitors the health, kinetic activity, and location of that animal and perhaps other animals in a herd. The battery of the bolus is continuously recharged in response to the peristaltic contractions of the rumen. The bolus communicates via a local network transmission technology such as Bluetooth to a radio transmitter mounted on the tail of the animal using a tail-mounted bracelet. This transmitter may then communicate the collected data and additional sensor data to the server. Thermal cameras mounted near water troughs, in corridors to milking rooms, or on drones may be used to
(Continued)

supplement the data collected by the bolus to provide data indicative of the health condition of the animal.

15 Claims, 15 Drawing Sheets

(51) Int. Cl.
*A61B 5/01* (2006.01)
*A61B 5/11* (2006.01)
*A01K 29/00* (2006.01)
*A61B 5/07* (2006.01)

(52) U.S. Cl.
CPC .............. *A61B 5/0008* (2013.01); *A61B 5/01* (2013.01); *A61B 5/073* (2013.01); *A61B 5/1112* (2013.01); *A61B 5/6861* (2013.01); *A61B 5/746* (2013.01); *A61B 2503/40* (2013.01); *A61B 2560/0219* (2013.01); *A61B 2562/0219* (2013.01); *A61B 2562/0271* (2013.01)

(58) Field of Classification Search
CPC ... A61B 5/073; A61B 10/0012; A61B 5/6861; A61B 90/98; A61B 5/746
See application file for complete search history.

(56) References Cited

U.S. PATENT DOCUMENTS

| | | | |
|---|---|---|---|
| 2009/0187392 A1* | 7/2009 | Riskey | A61B 5/4238 703/11 |
| 2014/0275863 A1 | 9/2014 | Gabriel et al. | |
| 2016/0353710 A1 | 12/2016 | Laporte Uribe | |
| 2017/0164580 A1 | 6/2017 | Rettedal et al. | |
| 2017/0215763 A1 | 8/2017 | Helfrich | |
| 2022/0104929 A1* | 4/2022 | Cummins | G16H 40/63 |

OTHER PUBLICATIONS

"International Application Serial No. PCT/US2019/018600, Written Opinion dated May 2, 2019", 3 pgs.

* cited by examiner

RUMINAL BOLUS FOR TRACKING BOVINES

CROSS-REFERENCE TO RELATED APPLICATIONS

This application is a U.S. National Stage Filing under 35 U.S.C. 371 from International Application No. PCT/US2019/018600, filed on Feb. 19, 2019, and published as WO2019/161397 on Aug. 22, 2019, which application claims the benefit of and priority to U.S. Provisional Application No. 62/632,158 filed Feb. 19, 2018, the entirety of which is incorporated herein by reference for any and all purposes.

TECHNICAL FIELD

Embodiments of the present disclosure relate generally to a system for monitoring the health, activity, and location of farm animals such as bovines. A bolus is inserted into the rumen of each bovine to collect health, kinetic activity, and location data of the animal that is communicated to a server that collects data for the entire herd. The peristaltic contractions of the rumen continuously recharge the battery.

BACKGROUND

Agricultural and animal farming has been increasingly automated in recent years to save labor costs. In the case of animal farming, for example, tagging techniques have been used to keep track of the location of the animals. However, the average herd control system is very expensive, quite invasive, and requires much human interaction to attach collars and pedometers that must be adjusted during the growth of the animal and that can get lost and damaged. Also, such collars can unfortunately represent a risk for the life of the animal due to accidental strangulation. Moreover, conventional herd control systems generally do not provide information about the health or activity of the animal. Such data is particularly important for sick animals or animals ready for breeding.

Systems have been described in the prior art that introduce boluses into the rumen of a bovine for providing time-released pharmaceuticals. Boluses have also been described that include sensors for monitoring temperature, pH, and other conditions of the animal. For example, U.S. Pat. No. 9,808,181 describes a system in which a bolus is inserted into the rumen to provide an ID for the animal as well as to collected data for use in calculating the digestive efficiency of the animal. Other systems such as those described in US 2007/0088194 introduce a bolus into the rumen to monitor pressure in the reticulum and to communicate the collected pressure data. Other systems, such as that described in EP 0897662, provide an ingestible bolus that monitors the core temperature of the animal. Still other systems, such as that described in US 2011/0181399, use energy harvesting with RFid tags to provide a passive RFid transponder that monitors the temperature of the animal and provides a unique ID for the animal. However, such systems do not provide a comprehensive way to cost-effectively monitor the health, activity, and location of cattle using a bolus that is recharged within the rumen and that provides for active monitoring of the animal by a user.

SUMMARY

Various details for the embodiments of the inventive subject matter are provided in the accompanying drawings and in the detailed description text below.

A system and method are provided that keep track of the health, kinetic activity, and location of an animal and provide an interface for active monitoring by a user. In one embodiment, a bolus is inserted into the rumen of a bovine and includes sensors for collecting the temperature, activity level, and location of the animal over time and circuitry for communicating the collected data to a server that monitors the health, kinetic activity, and location of that animal and perhaps other animals in a herd. The battery of the bolus is continuously recharged in response to the peristaltic contractions of the rumen. In some embodiments, the bolus communicates via a local network transmission technology such as Bluetooth to a radio transmitter mounted on the tail of the animal using a tail-mounted bracelet that is external to the animal. This transmitter may then communicate the collected data to the server. In other embodiments, the bracelet may be mounted on the animal's tail once the bolus has detected a diminished kinetic activity of the animal, a lowered ruminal activity, and a drop of the body temperature of the animal, as occurs 2 days before the calving by a bovine, for example. Since the tail-mounted bracelet is accessible, it may use a battery powered transmitter equipped with a rechargeable lithium battery or a conventional battery that would have a battery life of at least 30 days.

In other embodiments, the bolus data is supplemented by thermal images of the animals taken at animal congregation points like a water trough or a corridor to a milking room. In still other embodiments, thermal images are taken from the air by a drone. In each case, the thermal images are processed to identify the animal and the health condition of the animal based on, for example, temperature variations detected by the thermal images. The data is communicated to a user's app so that the user may remotely monitor the health and welfare of a particular animal or the entire herd.

In sample embodiments, a bolus is adapted for insertion into the rumen of a bovine and includes electronics comprising a temperature sensor, an accelerometer, a GPS module, a communication module, and a processing device that receives data from the GPS module, the temperature sensor, and the accelerometer and transmits the received data using the communication module. The bolus further includes a battery that powers the electronics and a battery recharging system that charges the battery in response to peristaltic contractions of the rumen. In sample embodiments, the battery recharging system comprises a sphere that separates a first magnet and spring encased in a coil of wire from a second magnet and spring encased in the coil of wire whereby any change in a magnetic environment of the coil of wire as the first and second magnets move apart from each other or closer together as a result of movement of the bolus causes a voltage to be induced in the coil. At least one voltage rectifier and a DC/DC regulator circuit processes the voltage induced in the coil for storage in the battery.

In other sample embodiments, the bolus further includes wings around an outer periphery of the bolus that are disposed beneath cellulose for insertion into the rumen whereby the wings expand once the cellulose has been degraded within the lumen. The bolus may also include a normally closed contact at one end of the bolus. The wing design increases the hydrodynamic resistance of the bolus and will allow it to be moved inside the rumen by every peristaltic contraction of the rumen.

In sample embodiments, the processor of the bolus comprises a low power microcontroller that receives the data from the GPS module, the temperature sensor, and the accelerometer and transmits the received data using the communication module at periodic intervals or in response to detection of an activity event by the accelerometer. The bolus may also include an antenna that enables communication between the bolus and one or more boluses of other bovines in a transmission range of the communications module to create an ad hoc mesh network.

In other embodiments, the bolus may be part of a broader system including a tail mounted bracelet that communicates with the bolus via a radio transmitter. The tail mounted bracelet includes a battery and sensors such as an accelerometer that monitors tail movements indicative of calving, for example. The tail mounted bracelet may further include a thermometer and circuitry that detects whether the tail mounted bracelet has fallen off the tail based on changes in temperature detected by the thermometer or changes in tail movements detected by the accelerometer. The tail mounted bracelet also may provide an alert signal when tail movements and/or temperature changes indicative of calving are detected.

In still other embodiments, the bolus is part of a system including a server that receives and stores the data transmitted by the communication module and provides an interface to a user device that enables the user to register the bolus, to specify who may receive alerts based on data from the bolus, to set alert options for those who may receive alerts, to select a type of data to be received from the bolus, and to monitor a status of multiple bovines having a bolus inserted in their rumen. The interface also may enable the user to set a geofence for a bovine receiving the bolus or for an entire herd. The bolus also may be linked to a unique RFid tag of the bovine.

In yet other embodiments, the bolus is used with a thermal camera that remotely detects kinetic activity and temperature of the bovine. The thermal camera may be mounted near a water trough or a corridor to a milking room. The thermal camera also may be mounted on a drone that may also include communications circuitry that interacts with the bolus of the bovine to download the data from the communication module.

As discussed herein, the logic, commands, or instructions that implement aspects of the methods described herein may be provided in a computing system including any number of form factors for the computing system such as desktop or notebook personal computers, mobile devices such as tablets, netbooks, and smartphones, client terminals and server-hosted machine instances, and the like. Another embodiment discussed herein includes the incorporation of the techniques discussed herein into other forms, including into other forms of programmed logic, hardware configurations, or specialized components or modules, including an apparatus with respective means to perform the functions of such techniques. The respective algorithms used to implement the functions of such techniques may include a sequence of some or all of the electronic operations described herein, or other aspects depicted in the accompanying drawings and detailed description below. Such systems and computer-readable media including instructions for implementing the methods described herein also constitute sample embodiments.

This summary section is provided to introduce aspects of the inventive subject matter in a simplified form, with further explanation of the inventive subject matter following in the text of the detailed description. This summary section is not intended to identify essential or required features of the claimed subject matter, and the particular combination and order of elements listed this summary section is not intended to provide limitation to the elements of the claimed subject matter. Rather, it will be understood that the following section provides summarized examples of some of the embodiments described in the Detailed Description below.

BRIEF DESCRIPTION OF THE DRAWINGS

Various ones of the appended drawings merely illustrate example embodiments of the present disclosure and cannot be considered as limiting its scope.

Figure 1:
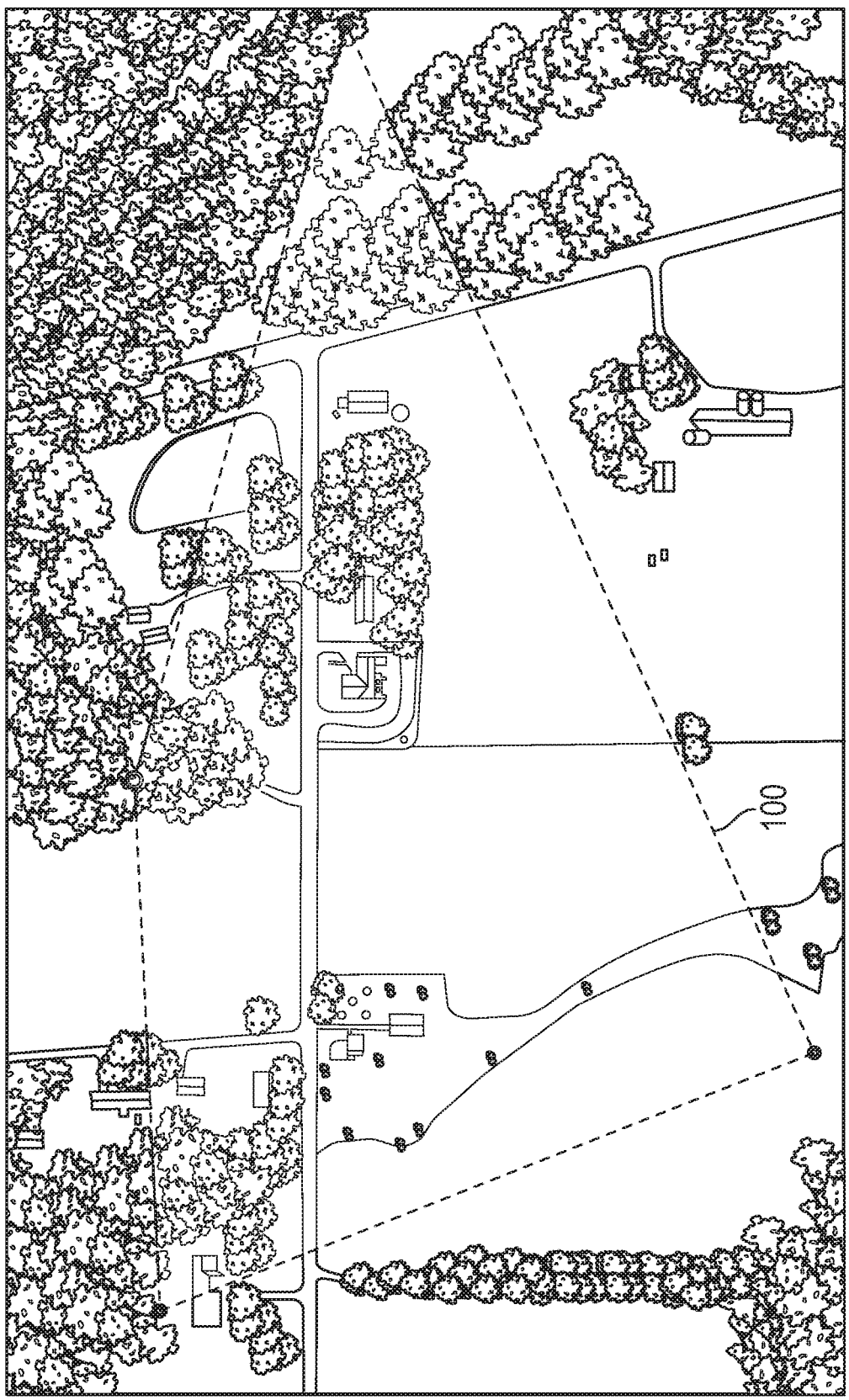
FIG. 1 illustrates a virtual fence that is integrated into the user's app whereby the user is alerted when an animal and/or the herd reaches the limit of a preselected geographic area.

The headings provided herein are merely for convenience and do not necessarily affect the scope or meaning of the terms used.

DETAILED DESCRIPTION

The description that follows includes systems, methods, techniques, instruction sequences, and computing machine program products that embody illustrative embodiments of the disclosure. In the following description, for the purposes of explanation, numerous specific details are set forth in order to provide an understanding of various embodiments of the inventive subject matter. It will be evident, however, to those skilled in the art, that embodiments of the inventive subject matter may be practiced without these specific details. In general, well-known instruction instances, protocols, structures, and techniques are not necessarily shown in detail.

Overview

A ruminal bolus including sensors, a GPS device, and a radio transmitter as described below is completely incorporated in a melted resin under vacuum in order to avoid the formation of moisture on the device as a result of a continuous change of temperature when the bolus in inserted, for example, in the rumen of a bovine. The weight of the bolus is designed to be between 115 grams and 200 grams and is selected so that the bolus will settle in the bottom of the rumen to avoid being expelled from the rumen. The external part of the bolus is covered with a 2-mm cover of cellulose. Once the bolus is "launched" into the rumen, the cellulolytic bacteria that are normally present inside the rumen will degrade the cellulose cover. Once the cellulose cover is fully degraded, two small resin/plastic wings (FIG. 4B) are released that will increase the hydrodynamic resistance of the bolus and will allow it to be moved inside the rumen by every peristaltic contraction of the rumen. As will be explained in more detail below, this movement of the bolus will allow its battery to be recharged by the peristaltic contractions of the rumen.

The information collected by the sensors of the bolus is sent through GSM text or other mobile communications protocol to a server. In turn, the server sends the collected information to an app of the farmer's computer or smartphone through email and normal text for a specific alert (e.g., a calving event, heat on a low fertility animal, health emergencies, etc.).

The bolus contains the following internal components that are all connected to an electronic board: Internet of Things (IoT)/GSM/GPS technology that monitors location and provides communications capabilities, at least one accelerometer that monitors kinetic movement, at least one thermometer that monitors temperature of the animal, an optional pH reader that monitors pH levels of the animal, a Bluetooth/radio transmitter, a battery, and a movement based battery recharge system.

IoT/GSM/GPS technology: The bolus includes circuitry that sends information related to the position, activity, and health of the animal through SMS, notifications on an app, and/or email. The information related to the kinetic activity of the animal is particularly important to recognize as increased or diminished activity of the animal during the day may be used to recognize when the cow is in heat (and ready for breeding) or to recognize when the cow is going to calve. Generally, the activity data is combined with the ruminal activity and the temperature monitoring, using algorithms that will recognize a calving event at least an hour in advance. The notification of the calving event is sent from the bolus to the server and then from the server to the farmer's computer or smartphone app, through a text message directly to the mobile phone of the farmer and also to all the mobile numbers that will be registered to the farmer's account. Every bolus is furnished with a SIM card that is activated once the bolus is registered under a specific account. For example, the SIM card may be an M2M SIM card that is adapted to receive signals from every mobile company worldwide and that provides access to a mobile network. Other data transmission systems may also be provided that are compatible with the low data rates used for IoT connections of the ruminal bolus. For example, SIGFOX is a network that employs Ultra-Narrow Band (UNB) technology that enables very low transmitter power levels to be used while still being able to maintain a robust data connection. The SIGFOX radio link uses unlicensed ISM radio bands and the exact frequencies can vary according to national regulations, but in Europe the 868 MHz band is widely used and in the US the 915 MHz band is used. The density of the cells in the SIGFOX network is based on an average range of about 30-50 km in rural areas and in urban areas where there are usually more obstructions and noise is greater the range may be reduced to between 3 and 10 km. Distances can be much higher for outdoor nodes where SIGFOX states line of sight messages could travel over 1000 km. The overall SIGFOX network topology has been designed to provide a scalable, high-capacity network, with very low energy consumption, while maintaining a simple and easy to rollout star-based cell infrastructure.

Another possible solution based on mobile network availability is the 3GPP family of LPWA (Low Power Wide Area Network) technologies that includes NB-IoT (Narrow Band IoT). This technology can address the majority of IoT applications in terms of wide range of throughput rates, cost and power consumption options. NB-IoT consumes more power than SIGFOX but less than normal GSM. Most of the radio device available for GSM is actually pin to pin compatible with the NB-IoT module to make it easy to change technology without the need to modify the bolus design.

BC95-G is a high-performance NB-IoT module which supports multiple frequency bands of B1/B3/B8/B5/B20/B28* with extremely low power consumption. The ultra-compact 23.6 mm×19.9 mm×2.2 mm profile makes it a perfect choice for size sensitive applications. Designed to be compatible with Quectel GSM/GPRS M95 module in the compact and unified form factor, it provides a flexible and scalable platform for migrating from GSM/GPRS to NB-IoT networks. Key Benefits of BC95-G include:

Compact-sized multi-band NB-IoT module
Ultra-low power consumption
Super high sensitivity
LCC package makes it easy for large volume manufacturing
Compatible with Quectel GSM/GPRS module, easy for future upgrading
Embedded with abundant Internet service protocols
Fast time-to-market: Reference designs, evaluation tools and timely technical support minimize design-in time and development efforts The GPS circuit of the bolus registers the distance covered by the animal during the day with an interval compatible with the duration of the battery and its recharging system. The number of miles covered by the animal will give a precise indication of the physiological state of the animal in order to evaluate the above-mentioned parameters. The position of every animal in the herd is important to track as the location of the herd's grazing is important to monitor. In sample embodiments, a virtual fence 100 of the type illustrated in FIG. 1 is integrated into the app whereby the farmer is alerted when an animal and/or the herd reaches the limit of a preselected geographic area. The app may also permit the farmer to identify the exact geographic position of the animal on a map to facilitate reaching the animals that need veterinary assistance or supervision or need to be reached for other reasons. The app will display a circle on the map where the animal is located. In the case that the GPS signal is too weak, in the eventual occasion that the animal might be in a partially covered area (e.g., city canyons, thick bush) or in totally closed spaces, the device will try to get the signal and every 2 hours it will issue a location-based service (LBS) position given by the triangulation of the telephone cells or triangulation based on the IoT antennas.

The bolus is provided with a radio transmitter, and every bolus will be able to communicate with another bolus with a radio signal (lower energy required), whereby the herd will be connected by the radio signal. The information captured by the bolus will be sent by one of the boluses to the server. For example, the bolus that will send the message will be the one with a fully charged battery and it may change each time based on the amount of recharging received by each battery. This approach preserves the data while maximizing efficiency of battery usage.

Accelerometer: The accelerometer provides data relating to ruminal activity and further provides potential information related to an eventual calving event. For example, in a pre-calving scenario the interruption of the ruminal activity is a relevant sign of a possible calving event. The accelerometer monitors the ruminal activity in such a way to provide data that will be used to evaluate the ruminal efficiency of every single cow and will be able to identify an eventual physiological problem imputable to the diet or the dietary management of the animal whether the animal is on a beef or dairy farm.

Thermometer: The thermometer is important because it can be used to recognize with an hour's advance warning a calving event for a bovine. All the animals in an intensive farm are normally synchronized and inseminated where the approximate date of the calving is known but not the exact moment and in many other farming scenarios the reproductive activity is left to the bull. The bolus for bulls is slightly different compared to the one used on the female animals and it will interact with the bolus of the female in order to detect the moment of the mating (a bull normally stays very close to a female animal anticipating heat 2 days of advance). The Bluetooth/radio interaction between the two boluses that will be constantly close to each other will highlight the possible day of conception and the paternity of a consequential pregnancy. When a cow has been in heat or when it has been inseminated by the bull, all the data will be directly registered on the database and the animal will not be considered pregnant until the next heat period. If the animal does not go back in heat after a month, the farmer will be notified about an eventual pregnancy imputable to that specific bull that was close to the potentially pregnant cow/heifer. For example, a display interface such as that shown in FIG. 9 may be provided to the farmer to enable the farmer to monitor the pregnancies of the animals in the herd at a glance.

The calving event is one of the most dangerous and delicate moments for a female bovine. The thermometer is used to detect some of the most relevant pathologies that cause an increase in the temperature. For example, like in the case of BRD syndrome (Bovine respiratory disease), a rising temperature is the first symptom detectable and normally the animal will show signs of fever 48 hours before showing any other symptom. Depending on the type of fever, it is possible to distinguish an infection caused by Gram+ or Gram− bacteria or a parasitic infestation. This is a very important reason to develop an algorithm capable of recognizing the nature of the pathogen. All this information is important to a farmer as a sick animal is an economic loss. The capability of detecting a sick animal and alerting the farmer directly with a notification on the famer's mobile phone and/or computer could prevent untreatable health problems.

pH reader: A pH reader is important to provide a strategic monitoring of the ruminal fermentations during the fattening phase when the risk of acidosis and correlated pathologies is higher. Again, a text alarm and a notification on the farmer's app would prevent economic loss for the farmer. Though not shown in the illustrated embodiments, the pH reader may be on the bolus with the other elements. However, in other embodiments, the pH reader is provided on a separate bolus that is launched into the rumen separately because the pH sensor after 5/6 months might need to be recalibrated, as the need for recalibration is a common problem with existing pH readers. The recalibration problem is caused by the capillaries of the animal as the capillaries of the animal get easily blocked by the ruminal liquid. In some embodiments, this problem can be addressed by using nanotechnology material that would not allow any solid residuum to remain inside the capillaries. In other embodiments, an LED spectrometer may be used to measure the animal's pH by the refraction of the light with the ruminal liquid content.

Bluetooth/radio transmitter: A Bluetooth/radio transmitter is used to connect the bolus to a tail mounted bracelet equipped with a rechargeable battery (e.g. lithium) and with an accelerometer that furnishes additional data useful to predict the calving moment. The bracelet is mounted on a tail of the cow once the bolus has detected diminished kinetic activity of the animal, a lowered ruminal activity, and a drop of the body temperature 2 days before the expected calving. As noted above, all of the cows in intensive farms are artificially inseminated, so the date of the calving is generally known. However, this system recognizes the calving event 1-2 hours before the calving event using the data of the bracelet integrated with the thermometer, ruminal accelerometer, and kinetic data related to the daily activity of the animal. The bracelet typically has a rechargeable lithium battery that typically will last a minimum of 30 days. Ideally, the activity of the tail is monitored at least every hour, so if the number of contractions of the tail increases during an interval of 60 minutes, it means that the animal is more than likely going to calve in 1-2 hours. In sample configurations, the bracelet has a magnetic mechanism that locks the bracelet on the tail and adapts itself to different types of tails in such a way as to prevent any overtightening and eventual damage to the tail of the animal. In an embodiment, the part of the bracelet that contacts the tail of the animal is made of a pillow containing a liquid gel. The bracelet is communicatively connected and registered to a specific bolus for the required time until the calving event occurs. After the calving event, the bracelet unit is registered and communicatively connected to another bolus in such a way as to be used on another pregnant cow. This registration is done through an accessible platform on the server or through the app of the farmer's mobile phone, tablet, or computer.

Tail Mounted Bracelet

Figure 2A:
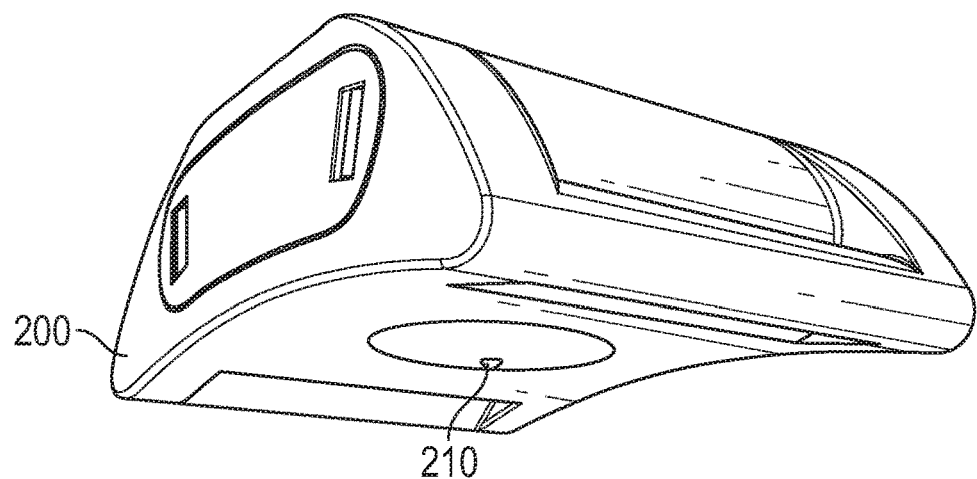
FIG. 2A illustrates a bottom perspective view of a sample embodiment of a housing of the tail mounted bracelet illustrating a temperature sensor at the bottom of the housing.
Figure 2B:
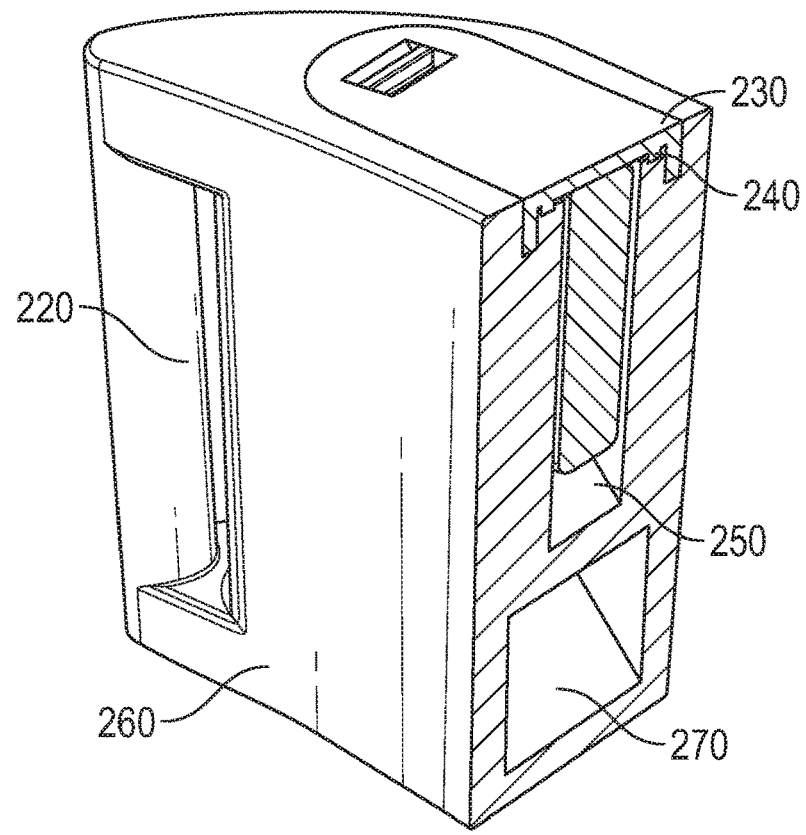
FIG. 2B is a cross-sectional view of the housing of the bracelet of FIG. 2A.
Figure 2C:
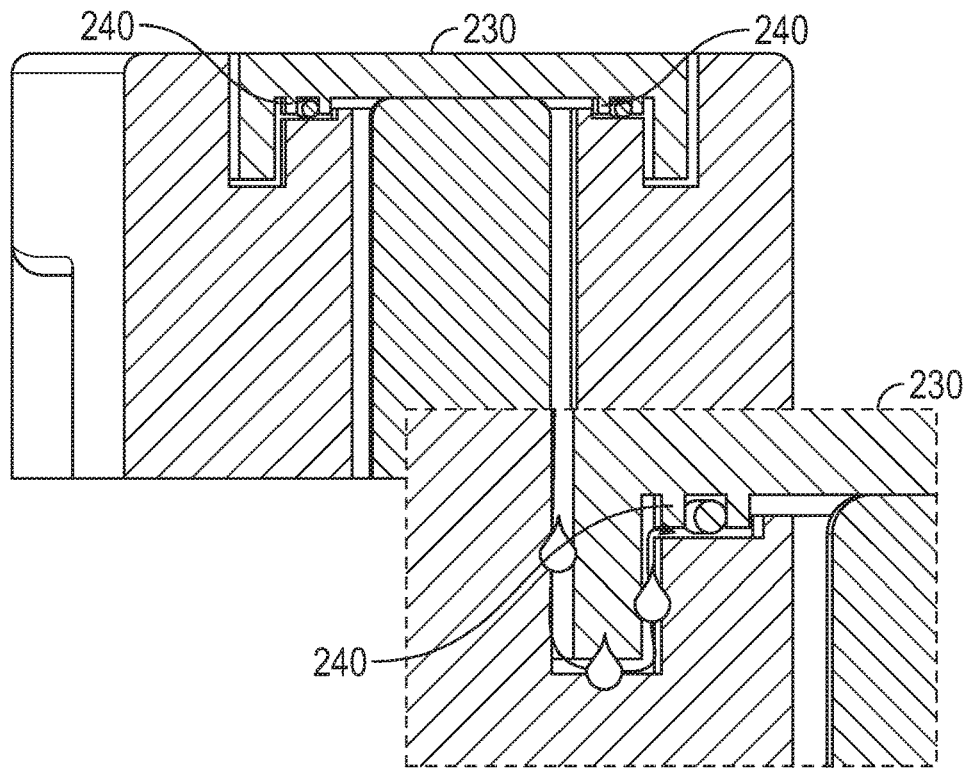
FIG. 2C illustrates a waterproof battery lid with a gasket that prevents water from getting into the battery slot.
Figure 2D:
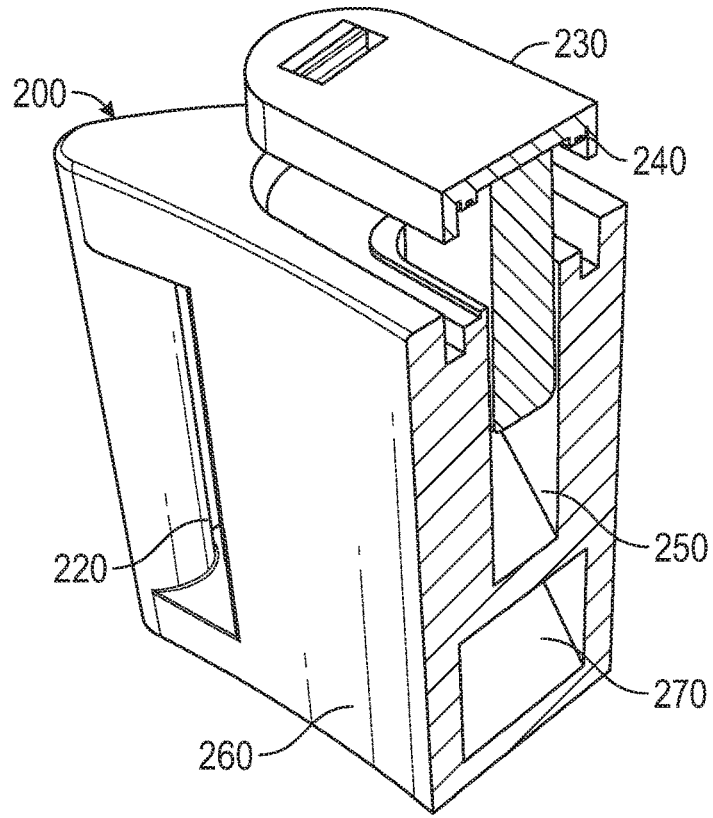
FIG. 2D illustrates the cross-section of the housing of FIG. 2B with the battery lid opened.

FIG. 2A illustrates a bottom perspective view of a sample embodiment of a housing 200 of the tail mounted bracelet illustrating a temperature sensor 210 at the bottom of the housing 200. FIG. 2B is a cross-sectional view of the housing 200 of the bracelet of FIG. 2A. As illustrated in FIG. 2B, the tail mounted bracelet housing 200 includes a belt guide 220 for attaching the bracelet to a belt for attachment to the animal's tail. A waterproof battery lid 230 is also provided with a gasket 240 (better shown in FIG. 2C) that prevents water from getting into the battery slot 250. The tail mounted bracelet also includes surface sensors 260 and a slot 270 for holding electronics as indicated. FIG. 2D shows the cross-section of the housing of FIG. 2B with the battery lid 230 opened.

An anti-fall system may also be provided in the circuitry of the tail mounted bracket that relies on the thermometer and on the accelerometer. For example, if the device on the tail is normally subjected to movements made by the animal, if the movements do not occur for a duration of 30 minutes or so, it will mean that the device has likely fallen from the tail. On the other hand, the thermometer may detect that the device is not attached at the tail as the thermometer will recognize the difference of temperature when the device is not on the animal.

Those skilled in the art will appreciate that the combination of the bolus and the tail mounted bracelet significantly increases the precision of the calving alert system to close to 99% as they together measure ruminal activity, temperature, kinetic activity of the animal, and movement of the tail which together are quite efficient in predicting a calving event. In some embodiments, the tail mounted bracelet transmits an alert signal to the server when a possible calving event is detected based on detected temperature changes and/or changes in tail movement.

As noted above, Bluetooth/radio interaction between the radios of respective animals is desirable to allow the radios with stronger batteries to transmit data as well as to permit communication with a special bolus inserted inside male bovines in order to monitor mating status. In fact, in the free gazing way of cattle farming, the breeding is normally left to natural mating of the animals. In such case, it is desirable to monitor when the bull stays close to the female that is going to be in heat. The interaction of the boluses of the bull and the female in heat in terms of distance and interaction related to the body kinetics of the animals will allow the monitoring software to identify the mating. The male bolus also may be connected to a collar that would give more precise information of the movements of the body that could be linked to the reproductive activity. In this case, the collar could be used in an intensive farm scenario rather than in an outdoor scenario. If the female that was mounted by a specific bull is not identified as being back in heat the following month, then these events could reasonably be correlated to a pregnancy including the paternity of the bull and the date of conception, which will enable a prediction of the date of birth of the future new-born calf.

The Bluetooth/radio also can be used to interact with each bolus of other animals in the surrounding area, which is helpful in the cases of a missing animal and to address problems related to poor GSM or GPS reception. In such cases, the last geographical position and the last interaction with the other boluses of the missing animal/bolus will be transmitted by another member of the herd once a GSM and GPS covered area is reached.

It will be appreciated by those skilled in the art that the radio communications capabilities of the boluses of respective animals may establish an ad hoc mesh communications network. As the bovine species normally live concentrated for strategic reasons (in nature they are prey and they like to stay together to defend themselves from eventual attacks), their behavioral peculiarity may be used to create a connection between the boluses. The reason for doing it is related to the efficiencies of the batteries and to spare energy. For example, the system may send the position of the entire herd by using a transmission of just one bolus at time, thereby enabling the boluses of the other animals to continue to recharge their batteries. On the other hand, if one of the animals strays from the herd, it can be considered a relevant ethological sign and the rest of the parameters and data collected by the bolus of the animal should be analyzed carefully because there might be a problem with the health/physiological condition of the animal. The position of one animal will be identified through GPS/LBS, while the position of the rest of the herd members is identified thanks to the radio signal identification and triangulation.

The type of network described above is an ad hoc mesh network. Those skilled in the art will appreciate that a mesh is a local network topology in which the infrastructure nodes (i.e. bridges, switches and other infrastructure devices) connect directly, dynamically and non-hierarchically to as many other nodes as possible and cooperate with one another to efficiently route data from/to clients. This lack of dependency on one node allows for every node to participate in the relay of information. Ad hoc mesh networks dynamically self-organize and self-configure, which can reduce installation overhead. The ability to self-configure enables dynamic distribution of workloads, particularly in the event that a few nodes should fail.

Bolus Charging System

Lithium battery: A normal rechargeable lithium battery may be used such as those commonly used for mobile phones. Of course, other types of batteries may be used that may hold sufficient charge for the purposes described herein.

Recharging battery system and reticulum-ruminal motility: An orderly pattern of ruminal motility is initiated early in the life of a bovine and, except for temporary periods of disruption, persists for the lifetime of the animal. These movements serve to mix the ingesta, aid in eructation of gas, and propel fluid and fermented foodstuffs into the omasum. If motility is suppressed for a significant length of time, ruminal impaction may result. A cycle of contractions occurs 1 to 3 times per minute. The highest frequency is seen during feeding, and the lowest when the animal is resting. Two types of contractions are identified. Primary contractions originate in the reticulum and pass caudally around the rumen. This process involves a wave of contraction followed by a wave of relaxation, so as parts of the rumen are contracting, other sacs are dilating. Secondary contractions occur in only parts of the rumen and are usually associated with eructation. The rumen in this case can be considered as an engine that produces kinetic energy due to its peristaltic activity. The amount of ruminal activity of a cow maybe monitored every day. In embodiments of the bolus described herein, the continuous contractions and the consequential peristaltic waves of the rumen are used to furnish a quantity of kinetic energy to the recharging system that is sufficient to fully recharge the battery of the bolus.

Figure 3A:
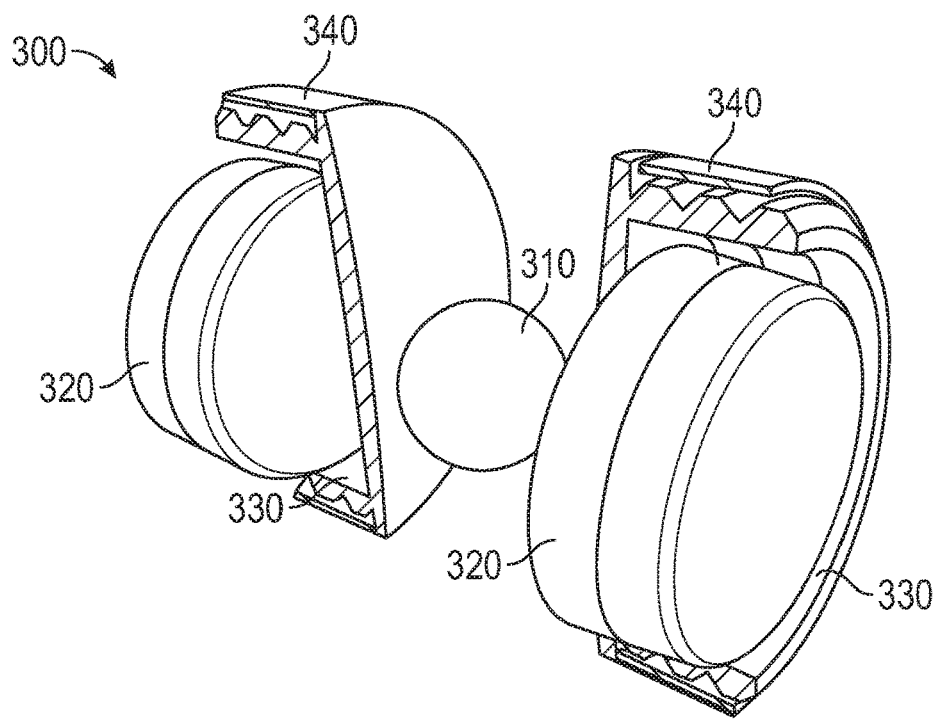
FIG. 3A illustrates an induction system including a bronze sphere that separates magnets and springs encased in a coil of wire.

For example, the induction system 300 illustrated in FIG. 3A includes a bronze sphere 310 that separates magnets 320 and springs 330 encased in a coil of wire 340 as illustrated. The induction system 300 is inserted into the bolus to generate electricity from the movement of the bolus in the rumen. In operation, any change in the magnetic environment of the coil of wire 340 as the respective magnets 320 move apart from each other or together causes a voltage (under Faraday's law, the emf voltage is proportional to the number of turns of the coil 340 and to the velocity of variation of the magnetic field) to be induced in the coil 340.

Figure 3B:
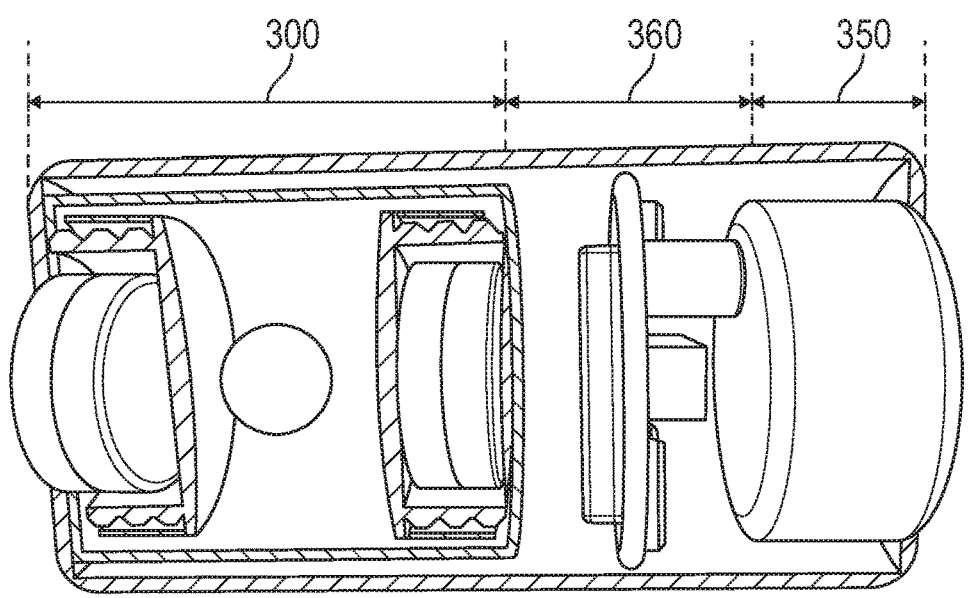
FIG. 3B illustrates a sample recharging battery system in a sample embodiment.

This change in the magnetic environment of the coil of wire 340 is produced by moving the coil 340 into or out of the magnetic field as a result of the peristaltic activity of the rumen. The resulting AC voltage is rectified, DC/DC regulated, and stored in the lithium battery 350 using conventional electronic circuitry 360 configured as shown in FIG. 3B.

Bolus

Figure 4A:
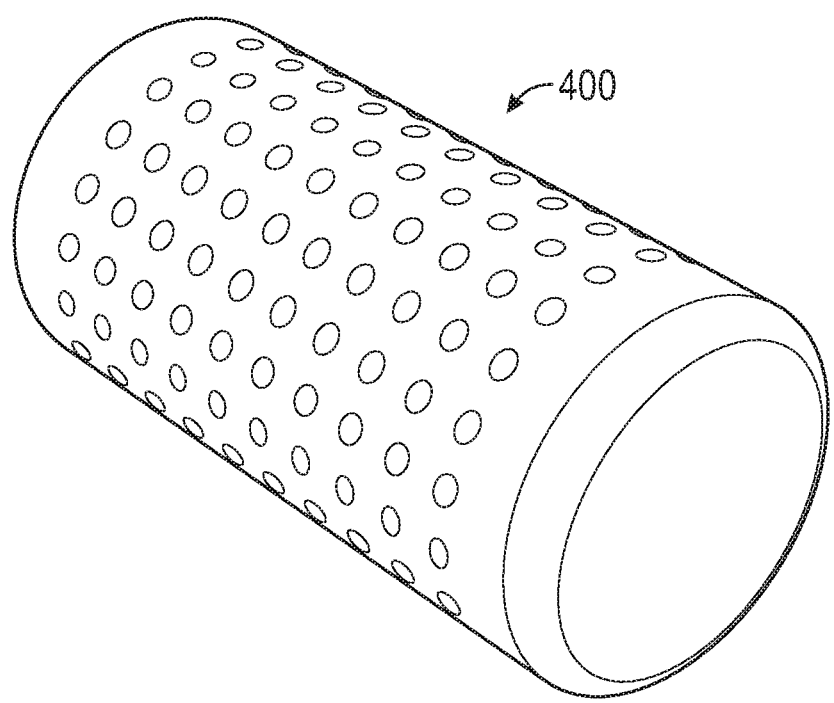
FIG. 4A illustrates a depiction of the outer surface of the bolus.
Figure 4B:
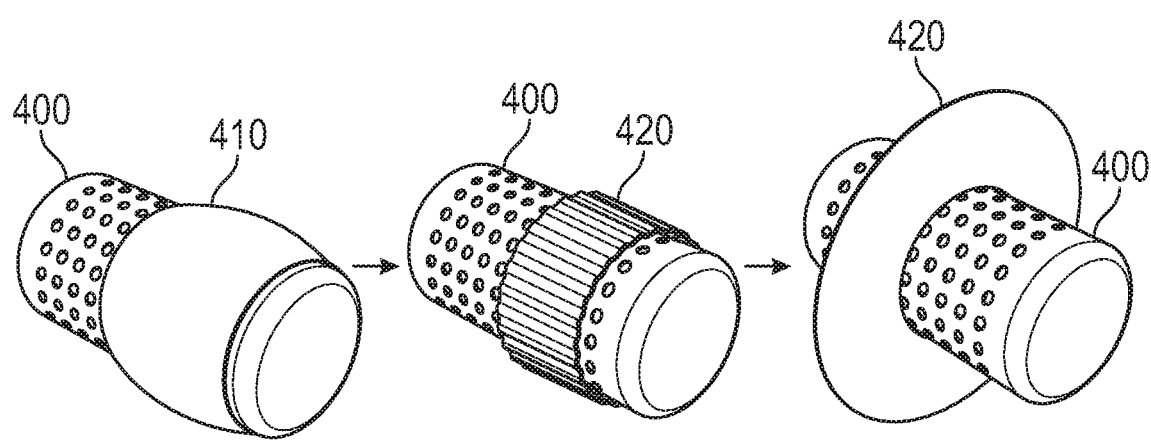
FIG. 4B illustrates the bolus of FIG. 4A with a cellulose cover over wings (left hand side), the wings once the cellulose has been removed (middle) and expanded wings (right hand side).
Figure 4C:
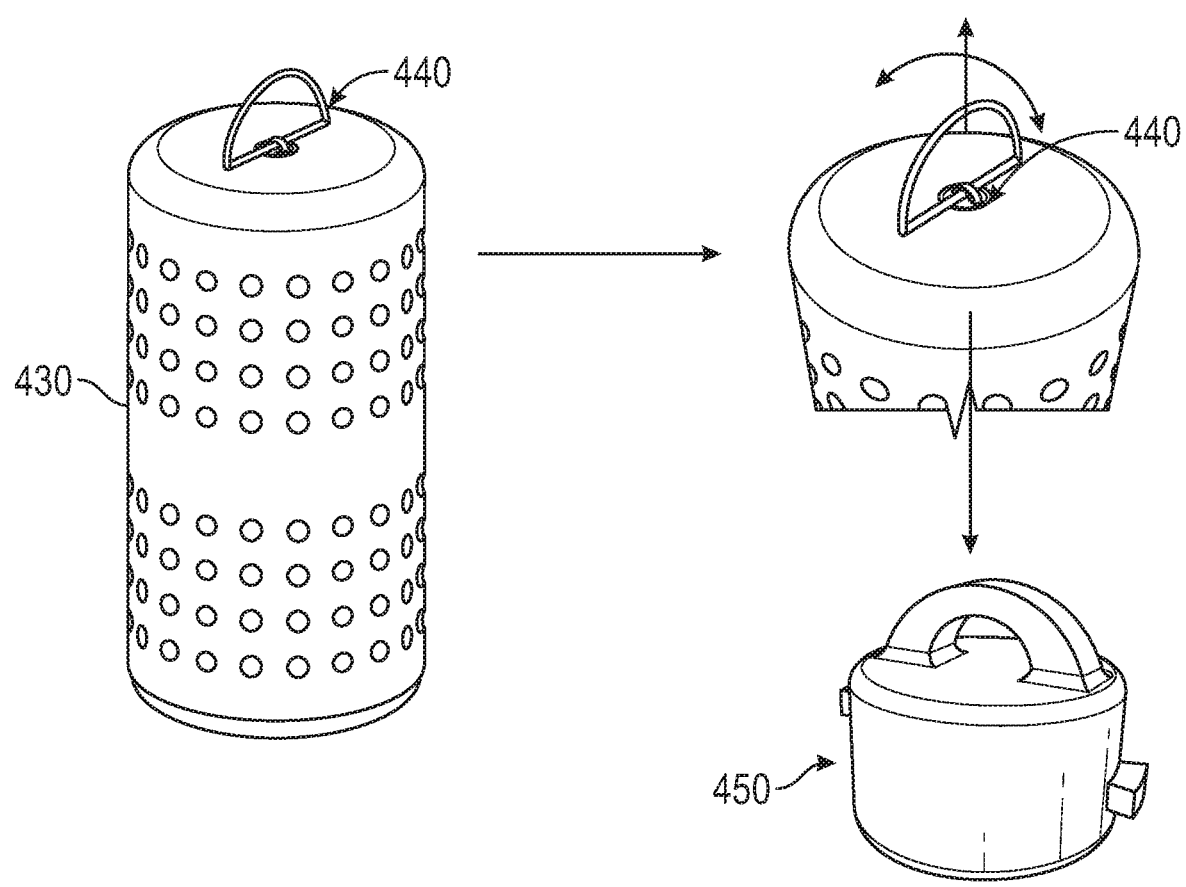
FIG. 4C illustrates an embodiment of a bolus with a normally closed contact inserted as a pin at one end.

FIG. 4A shows a depiction of the outer surface of the bolus 400. FIG. 4B illustrates the bolus of FIG. 4A with a cellulose cover 410 over wings (left hand side), the wings 420 once the cellulose has been removed (middle) and expanded wings (right hand side). As noted above, the expanded wings 420 increase the hydrodynamic resistance of the bolus 400 and will allow it to be moved inside the rumen by every peristaltic contraction of the rumen. FIG. 4C further illustrates an embodiment of a bolus 430 with a normally closed contact 440 inserted as a pin 450 at one end of the bolus 430.

Figure 5:
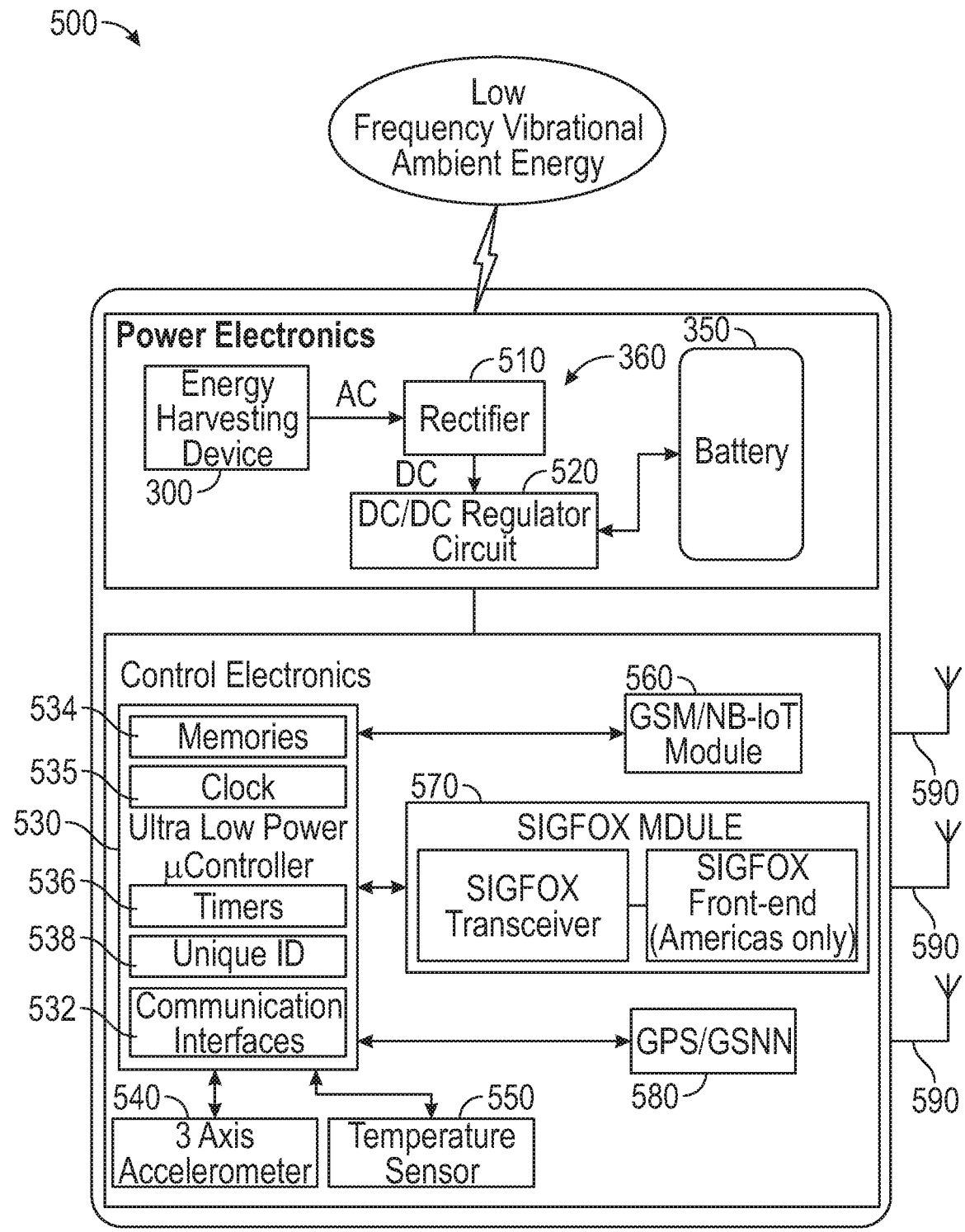
FIG. 5 illustrates a block diagram of a sample embodiment of the bolus electronics.

Bolus Hardware:

FIG. 5 illustrates a block diagram of the bolus electronics 500. As illustrated, the low frequency vibrational energy generated by peristaltic contractions of the rumen is captured by the energy harvesting device 300 shown in FIG. 3A and the resulting AC energy is rectified by rectifier 510, condensed, and provided to a DC/DC regulator circuit 520. The resulting regulated DC energy is stored in the battery 350. Power from the battery is provided to the control electronics of the bolus 400. As illustrated, the control electronics include an ultra-low power microcontroller 530 that receives sensor inputs from a 3-axis accelerometer 540 and a temperature sensor 550 through its communications interfaces 532. Though not shown, a pH reader may also be provided. The microcontroller 530 includes the appropriate memory 534, clock 535, and timers 536 to perform the functions described above and also includes a unique ID 538 that is used to tag and uniquely identify the generated data as from the corresponding bolus. The electronics further include the afore-mentioned IoT/GSM/GPS technology in the form of a GSM/NB-IoT module 560 and/or the SIGFOX module 570, as well as a GPS module 580 as illustrated. As better shown in FIG. 6, the bolus 400 also includes one or more antennas 590 that permit the bolus to communicate with other boluses of nearby animals to create an ad hoc mesh network as described above. The antenna(s) 590 may also enable communication with the tail mounted bracelet described with respect to FIG. 2.

Figure 6:
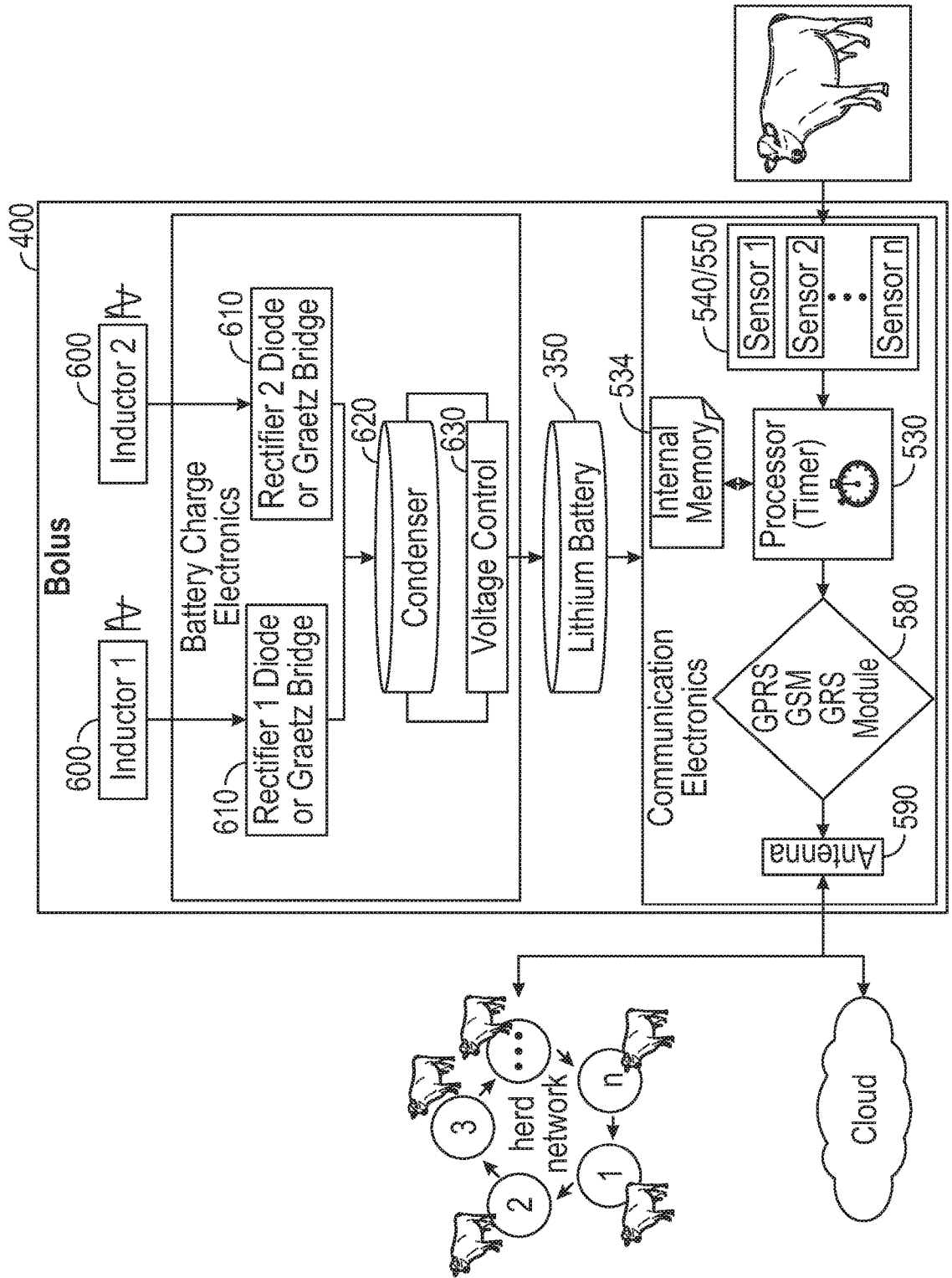
FIG. 6 illustrates a block diagram of the bolus electronics including an antenna that permits the bolus to communicate with other boluses of nearby animals to create an ad hoc mesh network.

As illustrated in FIG. 6, the bolus 400 may include one or more inductors 600 and one or more rectifiers (e.g., diode or Graetz bridge) 610 that provide AC energy to condenser 620 and voltage control circuit 630. The resulting regulated DC energy is stored in the battery 350. Battery 350 powers the communication electronics including sensors 540/550, processor 530, memory 534, GPS module 580, and antennas 590.

System Software: The system includes software within the bolus and the tail mounted bracelet as well as software at the server and in the user's app that operates on the user's smartphone and/or computer. The software on the user's smartphone and/or computer thus must be compatible with the operating system of mobile devices, tablets, and computer as appropriate.

Figure 7:
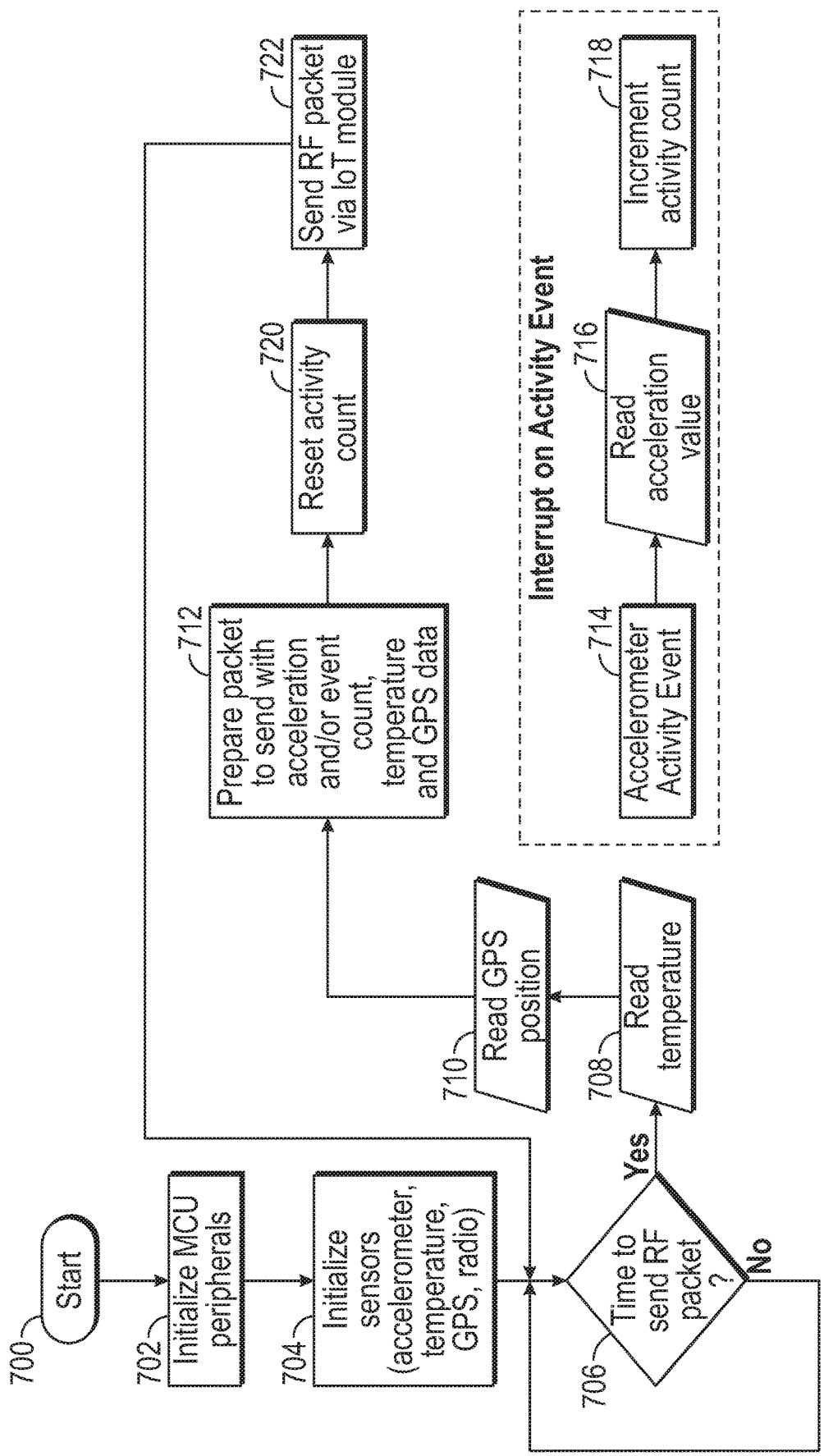
FIG. 7 illustrates a simplified flow chart of the operation of the bolus software that runs on the ultra-low power microcontroller.

FIG. 7 illustrates a simplified flow chart of the operation of the bolus software that runs on the ultra-low power microcontroller. As illustrated, the bolus software starts at 700 by initializing the peripherals at 702 and initializing the sensors including the accelerometer, thermometer, GPS, SIGFOX module, and GSM/NB-IoT module at 704. The software then waits at 706 until the designated time interval has passed for transmission of a data packet. In order to save energy, data packets are transmitted at designated intervals that may be on the order of milliseconds, seconds, minutes, hours, or days, as set by the timers of the ultra-low power microcontroller. When it is time to send a packet, the temperature and GPS position data are read at 708 and 710, respectively. The packet with the temperature and GPS data is then prepared for transmission at 712. The accelerometer data may be read or, as indicated, the accelerometer may provide data on an interrupt basis and provide the acceleration value for transmission when an accelerometer activity event is detected at 714. The accelerometer activity count may also be read at 716, incremented at 718, and sent with the packet. When the packet is ready to send, the activity count is reset at 720 and the resulting RF packet is transmitted via the GSM/NB-IoT module at 722. The software then waits the designated interval at 716 before repeating the process.

The tail mounted bracelet may also be adapted to include a similar ultra-low power microcontroller that processes software to read sensor data and transmit the collected sensor data at a designated interval.

Generally, the server software is accessible by the user (farmer) through a user name and password. Typically, all the operators working in the farm will have access to the password but typically there is a pre-selected master user that allows access by the secondary users. The server software registers the animals and the users and provides designated processing of the collected data.

Figure 8:
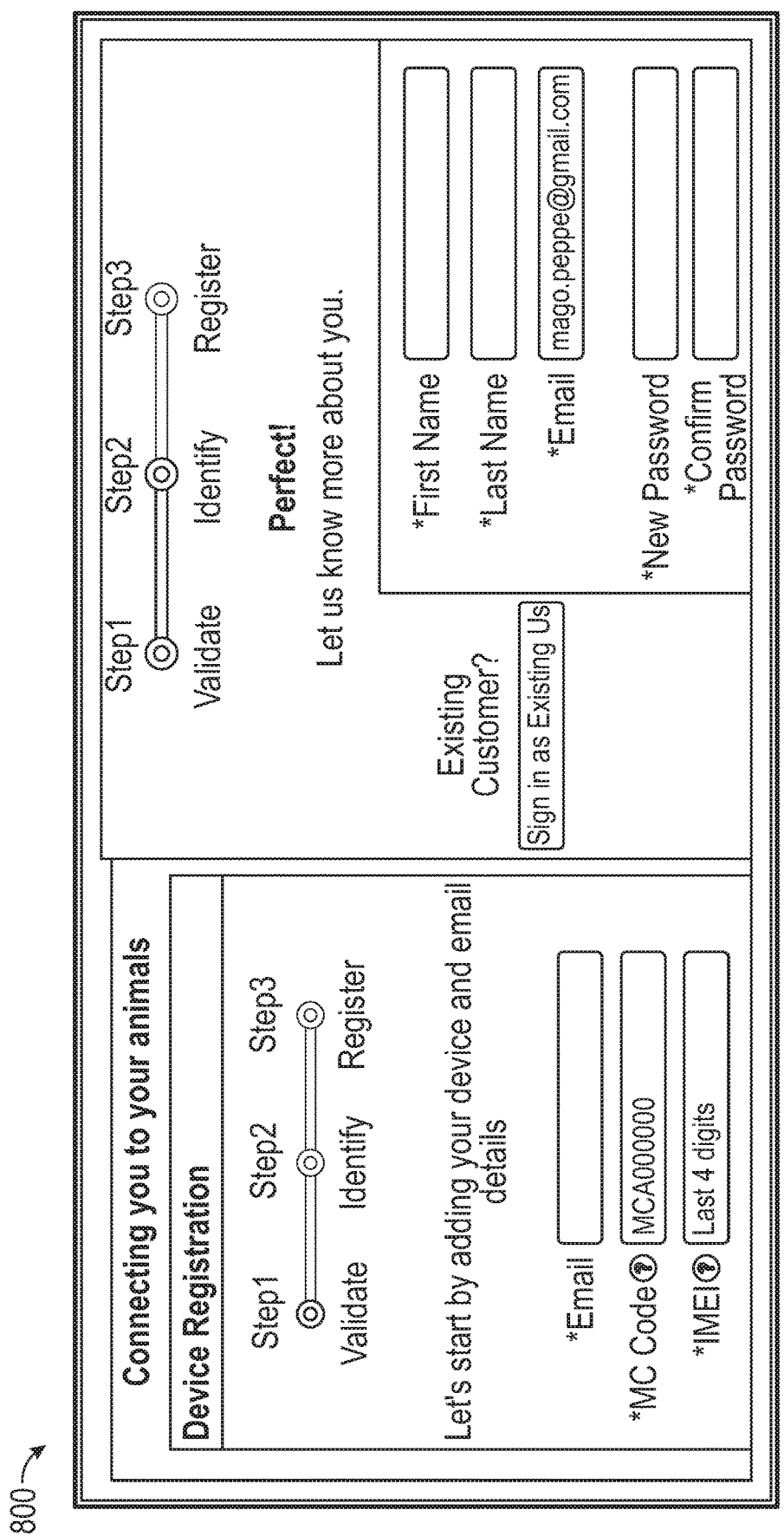
FIG. 8 illustrates a sample interface for registration of the bolus and user.

In some embodiments, every bolus 400 inserted into an animal is linked with 2 different codes—a BL code and an IMEI code related to the SIM card inside the bolus. The compatibility of the two codes allows the registration of the bolus under the user name of a specific client. This code compatibility for registration avoids any mis-typing of the numbers at the moment of the registration of the boluses. FIG. 8 shows an exemplary interface 800 for registration of the bolus and the user.

Every bolus 400 will have its own codes and is registered under a specific owner and herd number. This information is used for the identification of the animal. It will be appreciated that the bolus 400 might substitute for the conventional microchip system used for identification of animals by sanitation authorities as such microchips could be inserted directly into the bolus 400.

Figure 9:
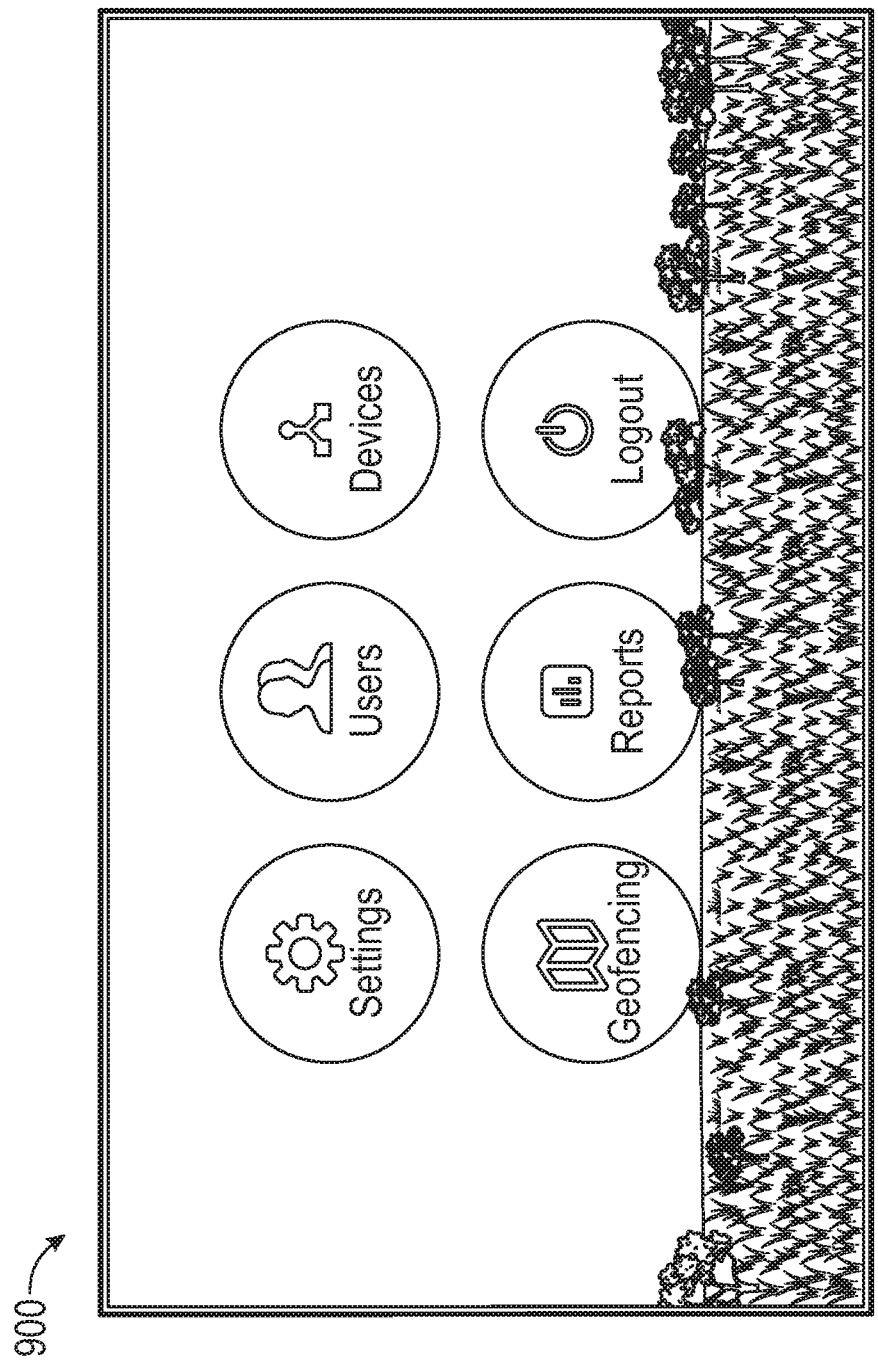
FIG. 9 illustrates an interface that enables the user to select the services and alerts the user desires in sample embodiments.

The server software also enables the user to decide which type of service he or she wants to use, and any additional function could be paid for separately. For example, if a farmer wants to use just the heat detection system, he or she would not pay for GPS capabilities, or vice-versa. The privacy and data treatment documents are accepted by the farmer at the moment of installing the app or downloading the software into his computer. A sample interface 900 for selecting the service options is shown in FIG. 9.

Figure 10:
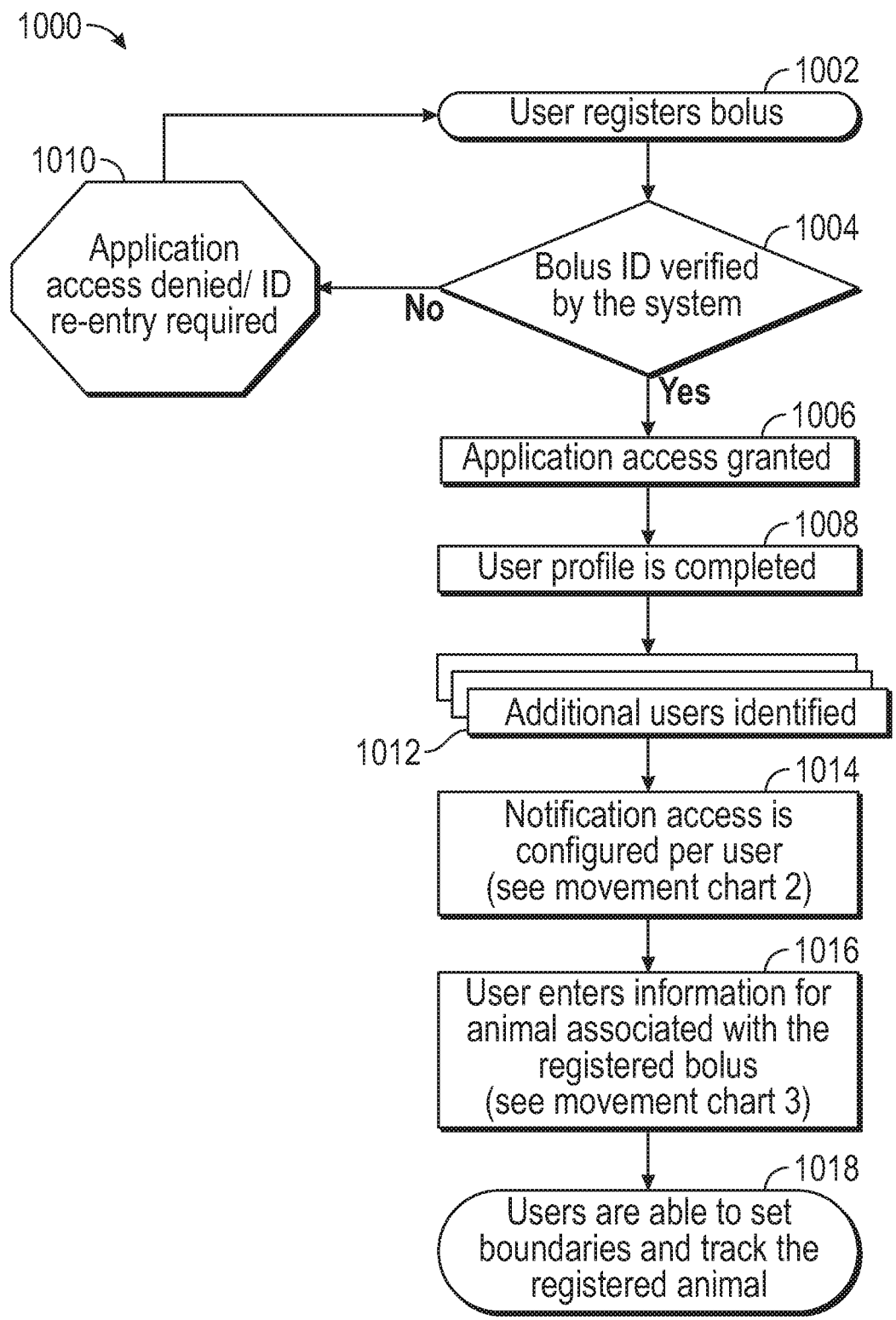
FIG. 10 illustrates the basic software process implemented between the server and the user's app in a sample embodiment.

FIG. 10 provides an overview of the basic software process 1000 implemented between the server and the user's app. As illustrated, the user first registers the bolus for an animal at 1002 and the bolus ID is verified by the system at 1004. Access to the system is only permitted at 1006 if the bolus ID is verified at 1004. If access is granted at 1006, the user is asked at 1008 to complete a user profile for each user of the system that is going to monitor the health and welfare of the animal receiving the bolus. Otherwise, the system denies access at 1010, and the user is again asked to register the bolus at 1002. The system enables the user to identify additional users at 1012 and to designate at 1014 how each user wishes to be notified if the bolus issues an alert relating to the animal's condition. The user may also enter information about the animal associated with the registered bolus to create a profile for the animal at 1016. The software also enables the user to set geofencing boundaries for tracking the registered animal as desired at 1018. The registered bolus is powered up and inserted into the animal for data collection.

Figure 11:
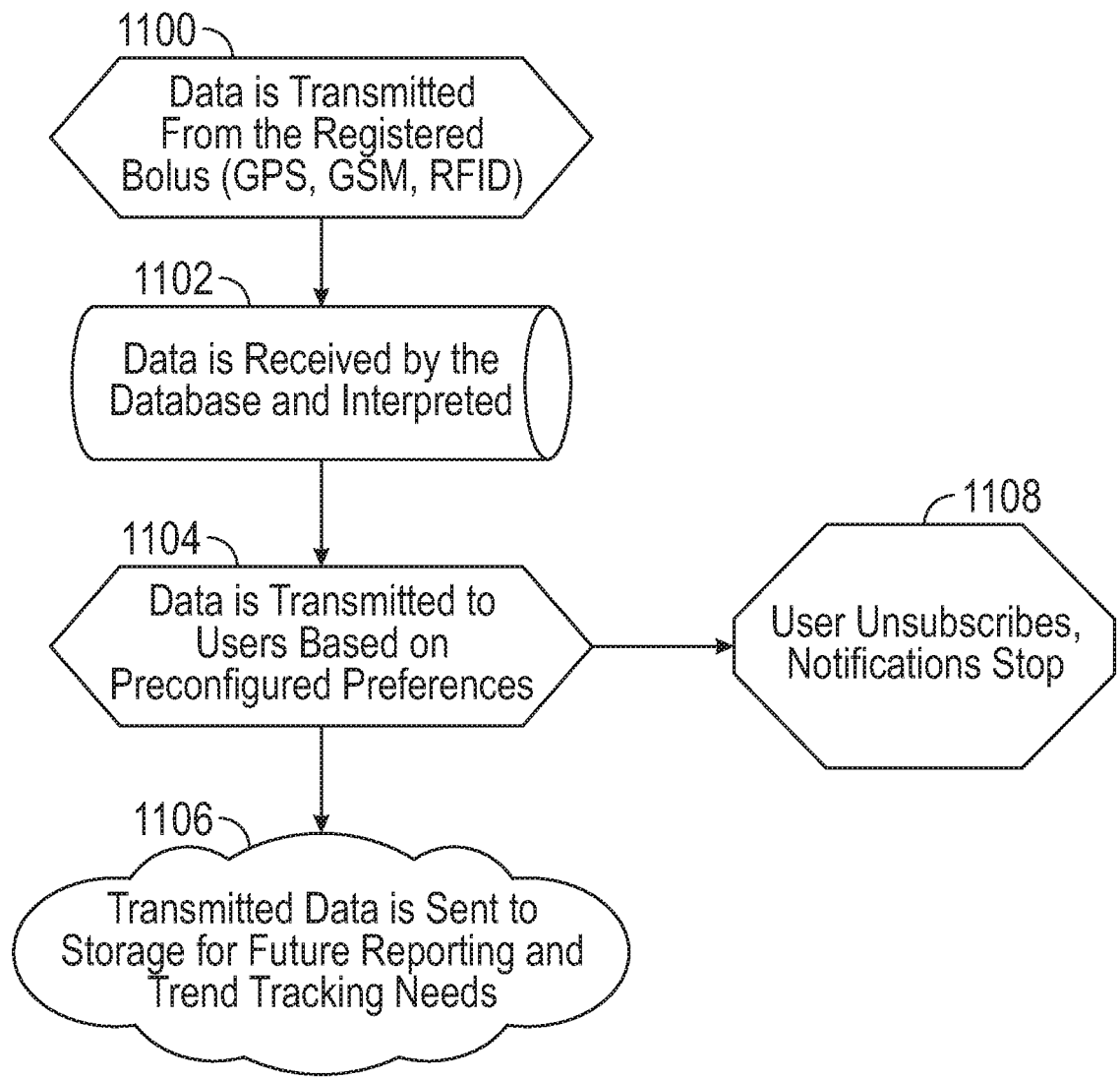
FIG. 11 illustrates the software process flow for alerting users in response to notifications from the bolus in a sample embodiment.

FIG. 11 illustrates the software process flow for alerting users in response to notifications from the bolus. As illustrated, data is transmitted from the registered bolus at 1100 and received at the server at 1102 where it is stored in a database for the registered bolus and is interpreted. If an alert is detected or if an alert is generated as a result of processing the received data, the alert signal is forwarded to the appropriate users at 1104 based on the alert preferences designated during the setup stage. The transmitted data is stored in the database for the registered bolus at 1106 and is used by report generation software of the server to generate animal status reports and to monitor health trends and the like of the registered animals. This process continues until the user unsubscribes at 1108.

Figure 12A:
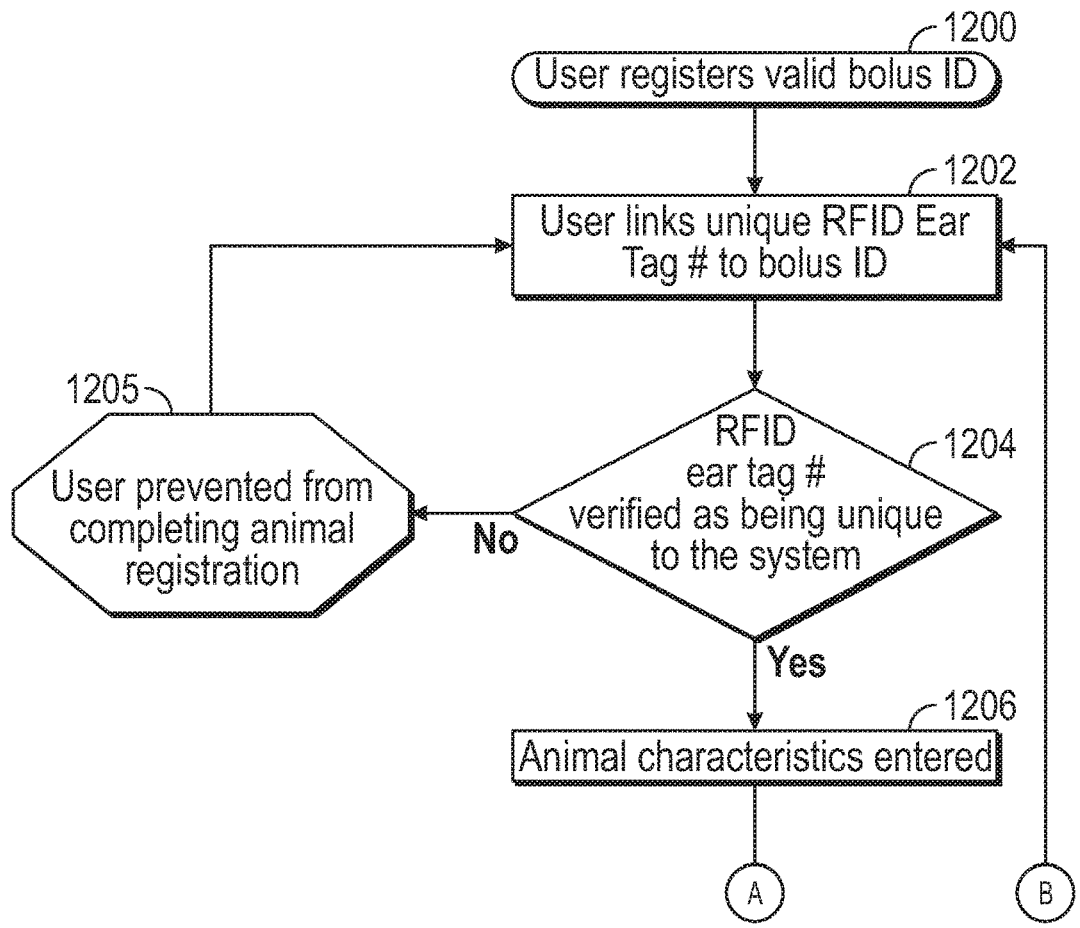
FIGS. 12A and 12B together illustrate the animal registration and tracking process flow of the server software in a sample embodiment.
Figure 12B:
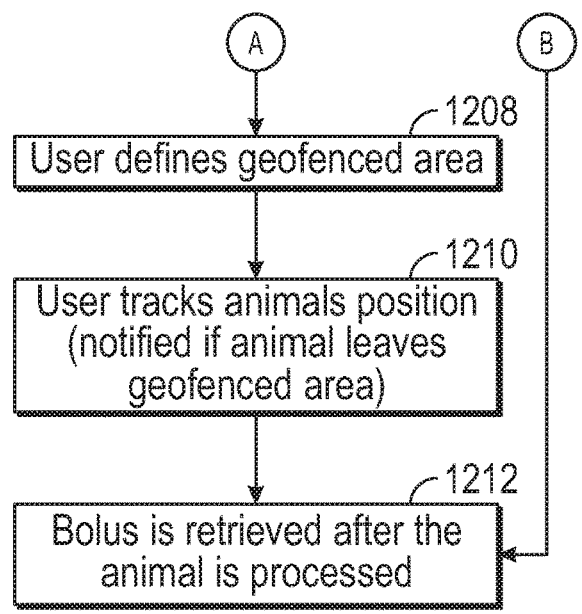

FIG. 12 illustrates the animal registration and tracking process flow of the server software. As illustrated, the user registers a valid bolus ID at 1200 and, where applicable, links the animal's unique RFid ear tag number to the bolus ID at 1202. If the RFid ear tag is verified as unique to the system at 1204, the user is enabled to enter the animal characteristics at 1206 and to define a geofenced area at 1208 as desired. If the RFid ear tag is not verified as unique to the system at 1204, the user is prevented from completing the animal registration at 1205, and the system control returns to 1202. The user may use the system to track the animal's position at 1210 and, when set up, the user may be notified if the animal leaves the geofenced area. The animal may continue to be tracked as described herein until the animal is processed and the bolus is retrieved at 1212.

In sample embodiments, the software interfaces with a herd management system to enable the detection of every problem related to health issues imputable to every single animal. All the information related to the quantity and number of infections, parasitic infestations, heat synchronization programs and vaccinal prophylaxis and epidemiologic scenario of the farm is collected and made available to the public health minister as appropriate. Specific user access may be provided for the veterinary practitioner working in the farm. The veterinary practitioner has access to more detailed data that might help with the identification of specific syndromes and symptoms and precisely identify the amount and the typologies of pharmaceutical products that the veterinary practitioner will need to use to treat the herd. In some embodiments, the veterinary practitioner data is monitored so that the activity of the veterinary practitioner may be monitored across farms and across time. For example, the veterinary practitioner's name, address, email address, specializations and interests are registered and monitored. In some embodiments, this registration permits products (e.g. animal pharmaceutical products) to be advertised/promoted to the veterinary practitioner. The data this captured also relates to antibiotic treatments, vaccine prophylaxis, anti-parasitic treatments, heat synchronization, embryo transfer, anti-inflammatory treatments, integrators of vitamins and minerals, and the like.

The GPS position of every single animal could be used as well for security and insurance company's policies. For example, the location of the animal is relevant in case of insured stolen livestock or eventual damage caused by an animal that escapes from a fenced area. The data collected by the ruminal bolus and by the herd management system is also relevant for integrators and feeding companies that are interested on evaluating the result obtained by their products or to have commercial information related to farms with which they desire to have a business relationship.

In other embodiments, a biometric recognition system is provided. For example, a facial recognition system is available on the app. The app has access to the camera of the phone in order to take a photo of the animal corresponding to the specific number of a specific bolus. The picture is unique as every animal is unique in terms of shape, eye distance and spots on the mantel. This identification system is more efficient than DNA testing as DNA testing will take more time, is more expensive, and the facial recognition would be immediate and enables the data to be sent to the department of agriculture. This approach has the additional benefit of minimizing scams related to the exchange of ear-tags that are common all over the world. With this system, the data is transmittable using a standard algorithm that measures the size, angle, eye distance, color of the eyes, spots, etc. in order to uniquely identify each animal. The information identifying each animal is kept in the cloud in sample embodiments and provided to the minister of agriculture in order to prevent scams.

Camera Imaging System

In other embodiments, a thermal camera and ruminal bolus are used together to identify animals and to monitor the behavioral patterns of the animals. Previously, the intensive farming industry has monitored animals using electronic devices such as collars and pedometers. Such devices, including the ruminal bolus devices mentioned above work with basic machine to machine communication techniques such as Wi-Fi® and RFid. However, conventional cattle management and monitoring systems are expensive and feature limited. A more robust system is desired that takes the system described above and applies artificial intelligence (AI) and self-learning machines to enable the remote monitoring of animal behavior.

Further embodiments of the system and method described herein incorporate a thermal camera system that provides input to the system to enable the server software to analyze and extract behavioral patterns and identify the peculiarities of each animal of the herd without necessarily needing to implant pedometers or collars on the animal. In such embodiments, the only device used on the animal is the bolus described above, though it will be appreciated that GSM capability is not necessarily required in such embodiments as a more suitable radio bolus may be used to transfer the information to small readers distributed around the intensive farm.

In such systems, the facial recognition system described above may be used to identify members of the herd in the field. For example, the facial recognition system for every member of the herd may be done manually through an app as discussed above or automatically using a camera situated at locations where the animals routinely pass (e.g. in a corridor through which the animals pass to reach the milking room). As noted above, every animal has a specific mantel with a unique pattern that will allow every animal to be uniquely identified from such images. Primarily, the animal's body and face is scanned and an ear-tag automatic number is captured and matched with the face of the animal. The collected data is transferred to a local or remote computer server using Wi-Fi® or through GSM technology (text message or 3G/4G/5G connection). In some embodiments, the data is sent to a cloud server and is accessible through the app on the user's smartphone or on the farm's computer.

Figure 13A:
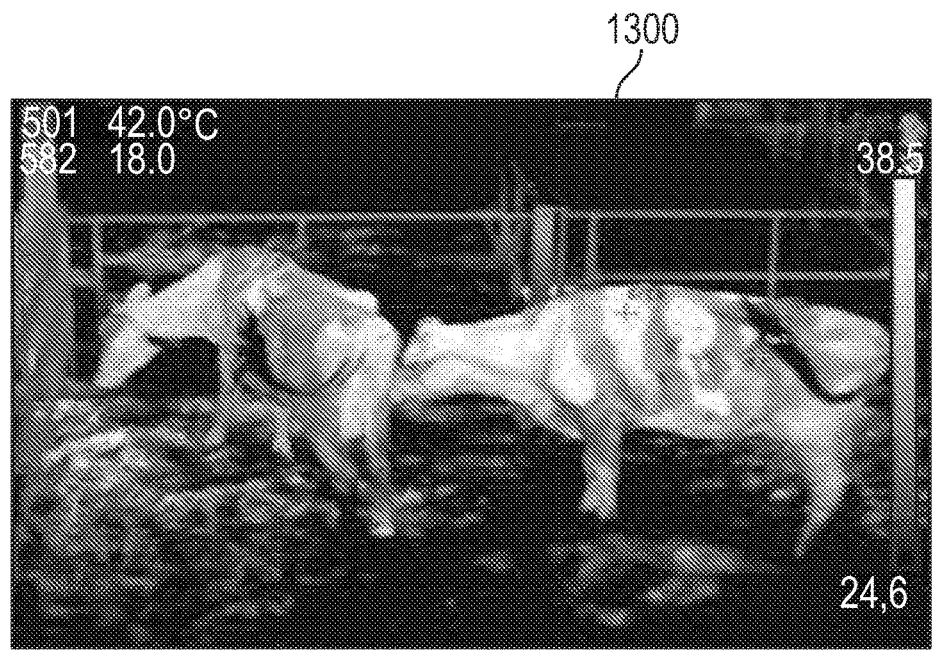
FIG. 13A illustrates thermal images of cattle as provided by a thermal camera.
Figure 13B:
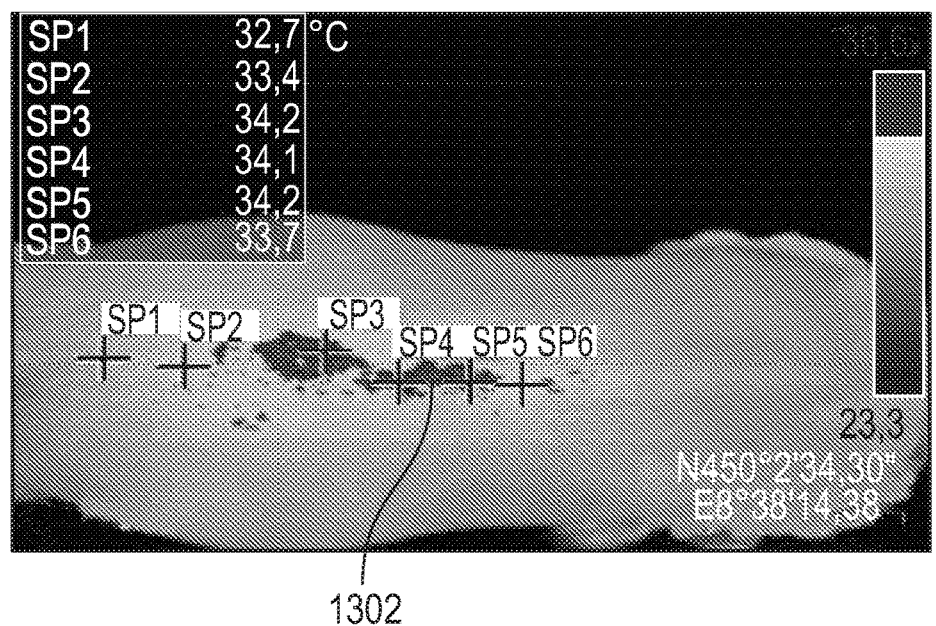
FIG. 13B illustrates how the thermal camera may identify hot spots within the animal.

The system is configured to identify bulls, heifers, cows, and calves through the identification parameters mentioned above and to alert the farmer if there is anything wrong with the animals. In some embodiments, the thermal camera is capable of remotely monitoring the animal's body temperature and alteration of the body temperature in specific parts of the body (mastitis). In such embodiments, a thermal camera may be implanted near the milking room and a robotic harm used to scan the mammary gland. In the same way, thermal variations of specific parts of the body of the animal be scanned and used to predict a calving event, infections and inflammations. For example, FIG. 13A illustrates thermal images 1300 of cattle as provided by a thermal camera, while FIG. 13B illustrates how the thermal camera may identify hot spots 1302 within the animal. Those skilled in the art will appreciate that conventional infrared thermography is sensitive enough to perceive changes in milk sample and skin surface temperature (SST) in response to varying degrees of severity of the mammary gland infection as reflected by the California Mastitis Test (CMT) score and milk quality, suggesting that as a non-invasive tool, infrared thermography also can be employed for screening dairy cows for mastitis.

In such embodiments, the bolus 400 described herein (with or without GPS or GSM capability) may be used to monitor ruminal activity (with accelerometer) and internal temperature (with thermometer) of the animal. The use of the bolus is less expensive than using a collar and a pedometer. In sample embodiments, the bolus 400 has a lithium battery that will be able to work a minimum of five years and/or the recharging battery system described herein may be used maximize and extend the life of the bolus.

In other embodiments, the camera system will remotely monitor the kinetic activity of the animals and will identify specific behavioral patterns that could lead to specific physiological moment, like heat detection/mating, alimentary period, fighting for the instauration of hierarchies, calving events, animal welfare monitoring, and the like. Such a system also may be adapted to monitor the stress level of the herd during human handling by identifying non-convenient maneuvers or inadequate handling of the herd by the operators.

The camera and the movement analyzing software also may identify lame animals and alert the farmer. The animal also may be added automatically to a lame cow register which will identify initial lame problems in the herd in order to minimize the usage of antibiotics in order to avoid antibiotic resistance.

A high stress level of the herd influences negatively the milk production of the animals. Other problems related to a high stress level could be related to overcrowded boxes as in specific times of the year farmers are so busy that they have difficulty in identifying these types of problems. The camera system described herein enables farmers to identify high stress behavioral patterns and alerts the farmer in order to prevent injuries and incidental loss of production.

Software associated with the thermal cameras may also be used to identify overheating of the animals during the hot season and will provide information needed to regulate the air conditioning of the farm in order to maintain in real-time an optimal temperature environment as possible. Such temperature regulation is a useful remedy to increase the milk yield, the metabolism of the animal, and fertility.

In some embodiments of the system described herein, different "download stations" are placed around the farm to download the data from the bolus (e.g., the download stations may be placed near by the drinker in each box as every animal passes there several times a day). The download box identifies the number of the bolus and the ear-tag of the animal and registers the bolus in the same manner as discussed above. In addition, the download station sends through a 3G/4G/5G SIM card the collected information to the cloud server. Ideally, the download station is plugged into a normal AC electrical energy outlet or is furnished with rechargeable batteries.

Those skilled in the art will appreciate that the scaffold of the bolus in such embodiments is the same as for the GPS/GSM bolus, the battery and the self-recharging system are the same, and the accelerometer and the thermometer are the same. The only difference is the absence of the GPS and the GSM features and the connectivity between the respective boluses. Also, the software and the alert system are the same as for the GPS/GSM bolus system.

Further embodiments of the system and method described herein may monitor the status of a herd using monitoring drones. For example, in semi-intensive farms where the animals are kept outdoors in electric fenced paddocks, a drone with a thermal camera may be used to monitor the herd. During spring time, summer time, and autumn, the herds in some countries like Ireland, U.K., New Zealand, France, and some regions like northern Italy, Poland, Romania, and other countries where semi-extensive farming systems are used are kept outdoors in controlled and fenced fields. A drone may be used to manage the herd using the identification and monitoring techniques described herein.

In a sample embodiment, a drone is placed on a base on safe and stable ground outside the fences. The drone lands and departs from the base. The base is mounted with solar panels and one or more chargeable lithium/graphene batteries (two batteries may be used so that one may be charged at home if the battery mounted on the drone base is not be sufficiently charged by the solar panels). The user of the drone will be informed when the battery is going low through a text message, email, app notification (ringtone as a phone call) in order to change the battery with the second one previously charged at home.

The app for controlling the animals is the same as described above except that instead of registering a bolus, a drone is registered using the same registration system as described above.

In operation, every animal is scanned and identified by the drone's camera and the drone includes communications circuitry that interacts with the bolus inside every cow of the herd in order to download the data from the animal using radio frequency transmission. As in the above embodiments, the collected data may be processed to detect fever and to identify specific types of pathogens by the type of fever, to detect heat or calving events, and rumination (monitoring of physiological ruminal activity and eventual calving event). The drone's thermal camera scans the face and the body of the animal, reads the ear-tag, and communicates with the bolus in order to download the data. The drone will register all the data and will pass to the next animal.

Once the drone is back to the base, the information is downloaded to a console and sent by 3G/4G/5G to the monitoring server. The software installed on the console (the console may be a miniaturized laptop, included in a waterproof and anti-shock sealed box) analyzes the data and monitors the herd's condition. The console also may transfer the data to the monitoring server, which will furnish all the data to each client account through computer access or smartphone app and will send alert text messages through text, app notification, email, and the like. In a sample embodiment, the console is located on the base of the drone and includes the software for communicating in 3G/4G/5G with the monitoring server. In some embodiments, the monitoring server is adapted to receive all the data collected by multiple drones used to service one or more herds. The software is generally the same as the software used in the intensive farm example given above.

The thermal camera of the drone registers the images of every animal, and every picture is named to indicate a specific animal. If there will be any alteration like a rise of temperature or the breathing frequency of the animal or a diminished body condition score of the animal, an alert message is sent to the user. All the parameters analyzed by the drone's camera are the same as those discussed above with respect to the fixed thermal camera used in an intensive farm system. Also, as with the other embodiments, the collected data may be used to identify mastitis, identification of infections on the navel in calves, and other maladies that may be tied to rising temperatures in specific areas of the bodies.

The geographical area that the drone will have to monitor is decided through multiple geofencing, through the user's app. Every geofence is named with a specific name by the user in order to identify different fenced lots of lands.

The drone registers every animal in every specific field in order to have access to every animal present on a specific lot of land. Infra-red stickers or marks may be placed on gates to monitor whether a gate is open or not. Also, to allow for the situation were a calf is hiding inside the rushes or the bushes, the drone may have infrared vision that is used to identify and monitor a new born animal. On the other hand, if the calf's presence cannot be registered in that field, the system would send a notification to the user.

In some embodiments, the drone includes anti-theft features whereby if the drone or the base is removed without the authorization of the user through the user's app or the online platform from the place it was originally installed, the drone will alert the user and will activate its GPS in order to track the base and the drone.

In other embodiments, the drone system may be used for security monitoring of rural areas as well. For example, the operators of the farm might wear specific watch or marked vestiaries (will be subject to scanning facial identification) and the vehicles used on the farm might wear specific marks or stickers with a specific pattern (different code/pattern/barcode on it) stickers or marks might be infrared visible. With its geofencing system, the drone surveys the perimeter and the area of a specific geofenced zone. If there is an intruder (human or animal predator) a text alarm might be sent. Sensors on the main roads or in specific zones of interest of the farm will activate the base of the drone through 3G/4G/5G radio communication. If the drone identifies an unidentified vehicle or person, it will record a video and will take a picture of the intruder. Once the drone reaches the base, it communicates the collected information to the console. The console analyzes the data and sends the necessary notification to the farmer through text message, notification on the app, and email. The perimeter or the area and the distance from the ground is decided by the user. Also, the camera of the drone may be connected directly by 3G/4G/5G to the mobile app of the phone of the user so that the user will be able to zoom in or out and will be able to manually record specific details.

EXAMPLE MACHINE ARCHITECTURE AND MACHINE-READABLE MEDIUM

Those skilled in the art will appreciate that in some example embodiments, the functionality described herein will be implemented by instructions stored on a machine-readable medium (e.g., a machine-readable storage medium) for processing by a processor that processes such instructions to perform any one or more of the methodologies discussed herein. For example, the cloud computer system of FIG. 6 or the drone console described herein may include one or more processors in an exemplary embodiment within which instructions (e.g., software, a program, an application, an applet, an app, or other executable code) are processed for causing the cloud computer system of FIG. 6 or drone console to perform any one or more of the methodologies discussed herein. For example, the instructions may cause one or more processors in the cloud computing system to execute the flow diagrams of FIGS. 10-12 and to implement monitoring functions and health tracking functions as described herein. The instructions transform the non-programmed machine into a particular machine programmed to carry out the described and illustrated functions in the manner described. In alternative embodiments, the server of the cloud computer system of FIG. 6 may operate as a standalone device or may be coupled (e.g., networked) to other machines. In a networked deployment, the machine may operate in the capacity of a server machine in a server-client network environment, or as a peer machine in a peer-to-peer (or distributed) network environment. The server machine may comprise, but not be limited to, a server computer, a client computer, a personal computer (PC), a tablet computer, a laptop computer, a netbook, a set-top box (STB), a personal digital assistant (PDA), or any machine capable of executing the instructions sequentially or otherwise, that specify actions to be taken by the server as described herein. Further, while only a single server machine is generally described, the term "machine" shall also be taken to include a collection of machines that individually or jointly execute the instructions to perform any one or more of the methodologies discussed herein.

The server machine as described herein may include processors, memory, and I/O components, which may be configured to communicate with each other such as via a bus. In an example embodiment, the processors (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may execute instructions to implement the processes described herein. The term "processor" is intended to include multi-core processor that may comprise two or more independent processors (sometimes referred to as "cores") that may execute instructions contemporaneously. The machine may include a single processor with a single core, a single processor with multiple cores (e.g., a multi-core process), multiple processors with a single core, multiple processors with multiples cores, or any combination thereof.

The memory/storage may include a memory such as a main memory, or other memory storage, and a storage unit, both accessible to the processors such as via a bus. The storage unit and memory store the instructions embodying any one or more of the methodologies or functions described herein. The instructions may also reside, completely or partially, within the memory, within the storage unit, within at least one of the processors (e.g., within the processor's cache memory), or any suitable combination thereof, during execution thereof by the machine. Accordingly, the memory, the storage unit, and the memory of processors are examples of machine-readable media.

As used herein, "machine-readable medium" means a device able to store instructions and data temporarily or permanently and may include, but is not be limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., instructions) for execution by a machine, such that the instructions, when executed by one or more processors of the machine, cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components may include a wide variety of components to receive input, provide output, produce output, transmit information, exchange information, capture measurements, and so on. The specific I/O components that are included in a particular machine will depend on the type of machine. For example, portable machines such as mobile phones will likely include a touch input device or other such input mechanisms, while a headless server machine will likely not include such a touch input device. It will be appreciated that the I/O components may include many other components that are not shown in the figures. The I/O components are grouped according to functionality merely for simplifying the following discussion and the grouping is in no way limiting. In various example embodiments, the I/O components may include output components and input components. The output components may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

Communication may be implemented using a wide variety of technologies. The I/O components may include communication components operable to couple the machine to a network or devices via one or more couplings. For example, the communication components may include a network interface component or other suitable device to interface with the network. In further examples, communication component may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices may be another machine or any of a wide variety of peripheral devices (e.g., a peripheral device coupled via a Universal Serial Bus (USB)).

Transmission Medium

In various example embodiments, one or more portions of the network including the server described herein may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, the network or a portion of the network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The instructions may be transmitted or received over the network using a transmission medium via a network interface device (e.g., a network interface component included in the communication components) and utilizing any one of a number of well-known transfer protocols (e.g., hypertext transfer protocol (HTTP)). Similarly, the instructions may be transmitted or received using a transmission medium via the coupling (e.g., a peer-to-peer coupling) to devices. The term "transmission medium" shall be taken to include any intangible medium that is capable of storing, encoding, or carrying instructions for execution by the machine, and includes digital or analog communications signals or other intangible medium to facilitate communication of such software.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. For example, the systems and methods described herein may be used not only in cattle intensive farming, but also in the pig farming industry, poultry, and horse reproduction businesses.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

What is provisionally claimed is:

1. A bolus adapted for insertion into the rumen of a bovine, the bolus comprising:
   electronics comprising a temperature sensor, an accelerometer, a GPS module, a communication module, and a processing device that receives data from the GPS module, the temperature sensor, and the accelerometer and transmits the received data using the communication module;
   a battery that powers the electronics; and
   a battery recharging system that charges the battery in response to peristaltic contractions of the rumen.

2. The bolus of claim 1, wherein the battery recharging system comprises a sphere that separates a first magnet and spring encased in a coil of wire from a second magnet and spring encased in the coil of wire whereby any change in a magnetic environment of the coil of wire as the first and second magnets move apart from each other or closer together as a result of movement of the bolus causes a voltage to be induced in the coil.

3. The bolus of claim 2, wherein the battery recharging system further comprises at least one voltage rectifier and a DC/DC regulator circuit that processes the voltage induced in the coil for storage in the battery.

4. The bolus of claim 1, further including wings around an outer periphery of the bolus that are disposed beneath cellulose for insertion into the rumen whereby the wings expand once the cellulose has been degraded within the lumen.

5. The bolus of claim 1, further comprising a normally closed contact at one end of the bolus.

6. The bolus of claim 1, wherein the processor comprises a low power microcontroller that receives the data from the GPS module, the temperature sensor, and the accelerometer and transmits the received data using the communication module at periodic intervals or in response to detection of an activity event by the accelerometer.

7. The bolus of claim 1, further comprising an antenna that enables communication between the bolus and one or more boluses of other bovines in a transmission range of the communications module to create an ad hoc mesh network.

8. A system comprising the bolus of claim 1 and a tail mounted bracelet that communicates with the bolus via a radio transmitter, the tail mounted bracelet including a battery and an accelerometer that monitors tail movements indicative of calving.

9. A system as in claim 8, wherein the tail mounted bracelet further includes a thermometer and circuitry that detects whether the tail mounted bracelet has fallen off the tail based on changes in temperature detected by the thermometer or changes in tail movements detected by the accelerometer.

10. A system as in claim 8, wherein the tail mounted bracelet provides an alert signal when at least one of tail movements and temperature changes indicative of calving are detected.

11. A system comprising the bolus of claim 1 and a server that receives and stores the data transmitted by the communication module and provides an interface to a user device that enables the user to register the bolus and to specify who may receive alerts based on data from the bolus, to set alert options for those who may receive alerts, to select a type of data to be received from the bolus, and to monitor a status of multiple bovines having a bolus inserted in their rumen.

12. A system as in claim 11, wherein the interface enables the user to set a geofence for a bovine receiving the bolus.

13. A system as in claim 11, wherein the bolus is linked to a unique RFid tag of the bovine.

14. A system comprising the bolus of claim 1 and a thermal camera that remotely detects kinetic activity and temperature of the bovine.

15. A system as in claim 14, wherein the thermal camera is mounted on a drone, the drone further comprising communications circuitry that interacts with the bolus of the bovine to download the data from the communication module.

* * * * *